(12) United States Patent
Star et al.

(10) Patent No.: US 6,951,761 B2
(45) Date of Patent: Oct. 4, 2005

(54) MEASUREMENTS OF MULTIPLE MOLECULES USING A CRYOARRAY

(75) Inventors: Robert A. Star, Bethesda, MD (US); Takehiko Miyaji, Rockville, MD (US); Stephen M. Hewitt, Potomac, MD (US); Lance A. Liotta, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 153 days.

(21) Appl. No.: 10/233,193

(22) Filed: Aug. 30, 2002

(65) Prior Publication Data

US 2003/0054342 A1 Mar. 20, 2003

Related U.S. Application Data

(60) Provisional application No. 60/316,544, filed on Aug. 31, 2001.

(51) Int. Cl.[7] .......................... G01N 1/36; G01N 1/00; G01N 1/30; A01N 1/02; C12Q 1/00

(52) U.S. Cl. .......................... 436/174; 436/8; 436/63; 435/1.1; 435/4; 435/5; 435/6; 435/7.1; 435/40.5; 435/91.1; 435/307.1; 435/810

(58) Field of Search .......................... 435/1.1, 4, 5, 6, 435/7.1, 40.5, 91.1, 307.1, 810; 436/8, 63, 174

(56) References Cited

U.S. PATENT DOCUMENTS

| | | | |
|---|---|---|---|
| 5,290,706 A | 3/1994 | Camiener | |
| 5,382,511 A | 1/1995 | Stapleton | |
| 5,416,029 A | 5/1995 | Miller et al. | |
| 5,763,170 A | 6/1998 | Raybuck | |
| 5,948,621 A | 9/1999 | Turner et al. | |

FOREIGN PATENT DOCUMENTS

| | | |
|---|---|---|
| JP | 10248599 | 9/1998 |
| WO | WO 99/44062 | 9/1999 |
| WO | WO 99/44063 | 9/1999 |
| WO | WO 01/18238 | 3/2001 |
| WO | WO 01/34842 | 5/2001 |

OTHER PUBLICATIONS

Arenkov et al., "Protein Microchips: Use for Immunoassay and Enzymatic Reactions," *Anal. Biochem.* 278:123–131, 2000.
Bowtell, "Options availabe–from start to finish–for obtaining expression data by microarray," *Nat. Genet.* 21:25–32, Jan. 1999.
Christendat et al., "Structural proteomics of an archaeon," *Nat. Struct. Biol.* 7(10):903–909, Oct. 2000.
Emili and Cagney, "Large–scale functional analysis using peptide or protein arrays," *Nat. Biotech.* 18:393–397, Apr. 2000.
Feng, "A protein microarray," *Nat. Struct. Biol.* 7(10):829, Oct. 2000.
Guschin et al., "Manual Manufacturing of Oligonucleotide, DNA and Protein Microchips," *Anal. Biochem.* 250:203–211, 1997.
Karow, "Spotted Arrays, Meet Sushi Arrays: Low Cost Gives Manufacturers Taste for These Chips," *BioArray News* 2(24):1 and 7, Jun. 14, 2002.
Karow, "Making Cheaper Alternatives to Spotted Arrays, Researchers Try Them Sushi Style," *ProteoMonitor* pp. 6–7, Jun. 17, 2002.
Lander, "Array of hope," *Nat. Genet.* 21:3–4, Jan. 1999.
Liotta and Petricoin, "Beyond the genome to tissue proteomics," *Breast Cancer Res.* 2:13–14, 1999.
Maxwell and Davis, "Differential gene expression in p53–mediated apoptosis–resistant vs. apoptosis–sensitive tumor cell lines," *PNAS* 97(24):13009–13014, Nov. 21, 2000.
MacBeath and Schreiber, "Printing Proteins as Microarrays for High–Throughput Function Determination," *Science* 289:1760–1763, Sep. 8, 2000.
A.S., "Cheap Chips, NIDDK," *Genome Technology* pp. 54 and 56, Jul. 2002.
Schreiber, "Target–Oriented and Diversity–Oriented Organic Synthesis in Drug Discovery," *Science* 287:1964–1969, Mar. 17, 2000.
Zhu et al., "Analysis of yeast protein kinases using protein chips," *Nat. Genet.* 26(3):283–289, Nov. 2000.
Zhu et al., "Cellular gene expression altered by human cytomegalovirus: Global monitoring with oligonucleotide arrays," *Proc. Natl. Acad. Sci. USA* 95:14470–14475, Nov. 1998.
Zhu and Snyder, "Protein arrays and microarrays," *Curr. Opin. Chem. Biol.* 5:40–45, 2001.
MacBeath and Koehler, "Experimental Procedures for Small Molecule Printing," http://www–schreiber.chem.harvard.edu/home/protocols/SMP_text.html, Aug. 11, 1999 (11 pages).

(Continued)

*Primary Examiner*—Ralph Gitomer
*Assistant Examiner*—Kailash C. Srivastava
(74) *Attorney, Agent, or Firm*—Klarquist Sparkman LLP

(57) ABSTRACT

This disclosure relates to CryoArrays, which permit the analysis of samples (such as protein, nucleic acid, virus, or cell samples) in arrays that are prepared at low temperatures. Because CryoArrays are constructed as a block of substantially columnar samples, the block can be sliced to provide a plurality of identical or substantially identical individual arrays. The individual arrays can be used for parallel analysis of the same array feature set, for instance with different probes or under different conditions. Also provided are methods of making CryoArrays, devices for making CryoArrays, and kits.

18 Claims, 6 Drawing Sheets

OTHER PUBLICATIONS

"Genome Wonderland Gives Way to Daunting Challenges of the Proteome," *Howard Hughes Medical Institute—News* http://www.hhmi.org/news/fields2.html, Feb. 11, 2001 (4 pages).

"Genomic Analysis of Protein Function," *Howard Hughes Medical Institute—In the Lab* http://www.hhmi.org/research/investigators/fields.html, Feb. 11, 2001 (3 pages).

"Protein Chips Offer Powerful Method for Probing Protein Function," *Howard Hughes Medical Institute—News* http://www.hhmi.org/news/schreiber.html, Sep. 8, 2000 (3 pages).

"Chemical Genetics," *Howard Hughes Medical Institute—In the Lab* http://www.hhmi.org/research/investigators/schreiber.html, Dec. 27, 2000 (3 pages).

" 'Protein chips' offer powerful method for probing protein function," *EurekAlert* http://www.eurekalert.org/releases/hhmi–pco090600.html, Sep. 8, 2000 (2 pages).

Miyaji et al., "CryoArray, a new platform for proteomics on recombinant and native proteins," *2001 ASN/ISN World Congress of Nephrology* DATE (5 pages including schedule).

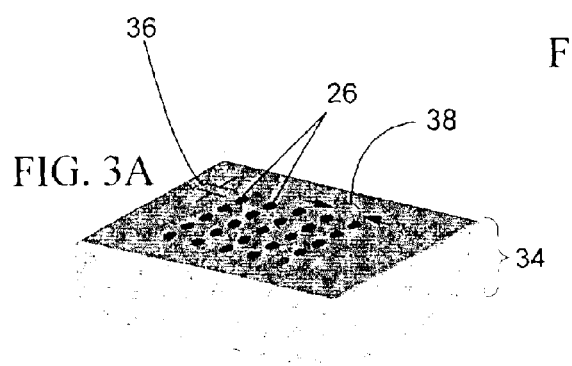
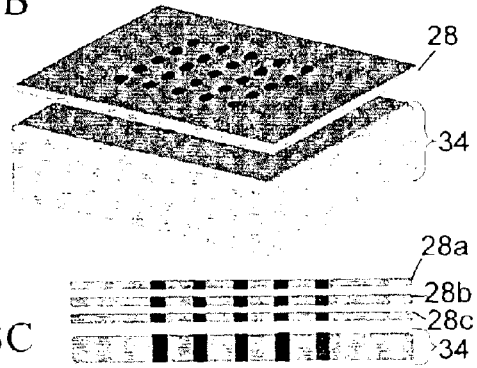
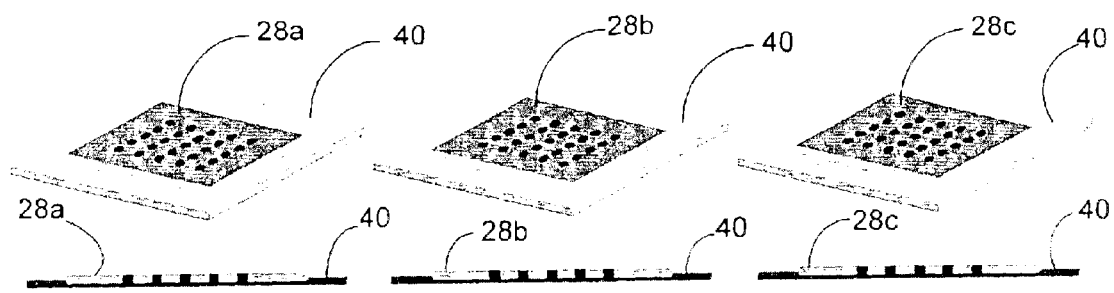
FIG. 3A  FIG. 3B  FIG. 3C
FIG. 3D  FIG. 3E  FIG. 3F

US 6,951,761 B2

MEASUREMENTS OF MULTIPLE MOLECULES USING A CRYOARRAY

PRIORITY CLAIM

This claims the benefit of U.S. Provisional Patent Application No. 60/316,544, filed Aug. 31, 2001, which is incorporated by reference herein in its entirety.

FIELD

This disclosure relates to medium to high-throughput methods for molecule analysis, particularly parallel measurement of nucleic acids, proteins, and antibodies using a cryoarray.

BACKGROUND OF THE DISCLOSURE

Recent advances in genomics, including SAGE and DNA microarrays, have allowed researchers to perform high throughput analysis of gene expression. These experiments generate large amounts of information, which must be confirmed by independent techniques one gene at a time. Cellular activity and function are controlled by protein activity, which cannot be easily predicted from measurement of steady state mRNA levels. Under some conditions, for example, increases in mRNA levels do translate to increased protein abundance. However, under some stresses, elevated mRNA levels are required to keep protein levels constant (Ideker et al., Science 292:929–934, 2001).

New techniques are being used to study cellular protein expression and function. For example, tissue arrays constructed to hold hundreds of tissue profiles from normal and diseased tissues can be sectioned, with each section being used to evaluate a different disease marker by immunohistochemical staining. This technique requires solid tissue samples, and antibodies that bind to formalin-fixed paraffin-embedded samples. Also, the target features of the tissue must be adequately represented within a 100–300 micron spot. The cellular heterogeneity of the kidney makes it difficult to ensure that even one glomerulus is contained within each sample.

Many techniques have been developed to study protein expression; however, they require expensive equipment (2-D mass spectroscopy, Ideker et al., Science 292:929–934, 2001; Ciphergen ProteinChip; Weinberger et al., Pharmacogen. 1:395–416, 2000; protein arrays, Paweletz et al., Oncogene 20:1981–1989, 2001, for instance), or prolonged or proprietary chemistry to attach proteins to solid support (for instance, with protein chips, see Zhu et al., Nat Genet. 26:283–9, 2000). Inexpensive hand stamping methods have been developed and are available commercially; however, only one or two arrays can be made at a time.

SUMMARY OF THE DISCLOSURE

This disclosure provides methods of making and using CryoArrays, arrays of biological samples (such as nucleic acids, proteins, cells, cell fragments, viruses, and biological fluids) prepared at low temperature and with minimal amounts of samples. CryoArrays are constructed as a block containing elongated, substantially columnar samples that are injected into a preformed cryoblock to form a loaded cryoblock. The loaded cryoblock is sliced or sectioned, for example, substantially perpendicularly to the elongated axis of the samples, to provide a plurality of corresponding arrays (cryosections), for example identical or substantially identical individual arrays.

Production of many corresponding or substantially identical CryoArray sections is simple, relatively inexpensive, efficiently uses samples with very little waste, and requires only a small volume of sample. The ability to make multiple cryosections from one cryoblock enables parallel analysis of many substantially identical arrays. Individual array sections can be used for parallel analysis of the same set of array features, for instance with different probes or under different conditions. Production of CryoArrays is a process that is less harmful to biomolecules, particularly proteins, because samples are kept frozen or near freezing during production of the cryoblock.

Specific examples and classes of CryoArrays are provided, including protein-based CryoArrays, nucleic acid-based CryoArrays, cell-based CryoArrays, delivery CryoArrays, virus-based CryoArrays, and sample-based CryoArrays. Methods of making and using these classes of arrays are described herein.

The foregoing and other features and advantages will become more apparent from the following detailed description and accompanying drawings.

BRIEF DESCRIPTION OF THE FIGURES

FIG. 1 shows a schematic drawing of an example CryoArray block.

FIG. 3 shows a schematic overview of the construction of a CryoArray, and cutting and removing of three individual sections from the array block.

FIG. 5 illustrates the fabrication of an example of a CryoArray block and individual section.

FIG. 6 shows a series of images of proteins detected from CryoArrays; the series illustrates optimization of bonding sample to a cryoblock. Cryoblocks were filled with either fluorescently labeled IgG (FIG. 6A) or recombinant PSA (FIG. 6B, FIG. 6C, and FIG. 6D), and samples detected by either fluorescence (FIG. 67A) or immunohistochemistry (FIG. 67B, FIG. 6C, and FIG. 6D).

DETAILED DESCRIPTION

Figure 1A:
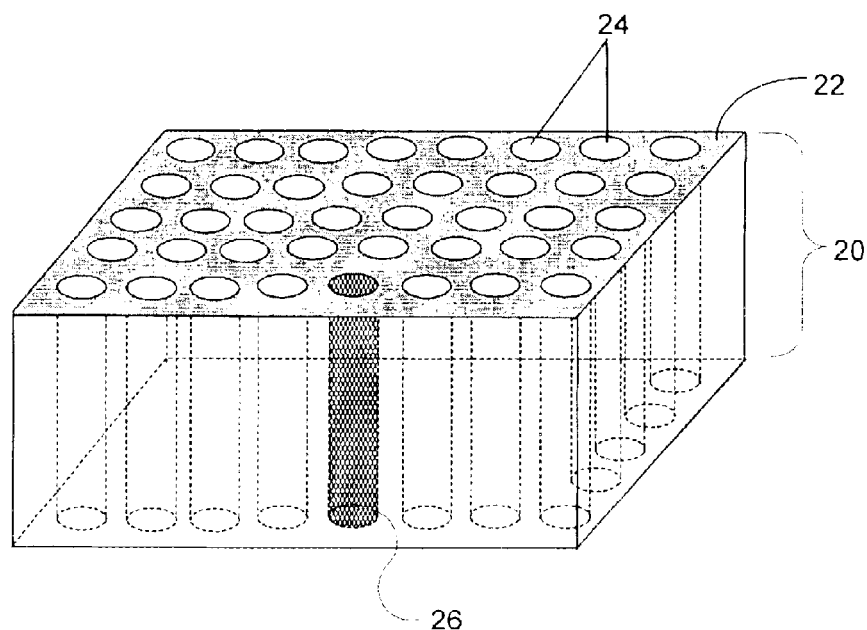
FIG. 1A shows the cryoblock.

I. Abbreviations cDNA: complementary DNA
CGH: comparative genomic hybridization
DNA: deoxyribonucleic acid
EST: expressed sequence tag
LCM: laser capture microdissection
OCT: optimal cutting temperature (embedding compound)
PSA: prostate specific antigen
SAGE: serial analysis of gene expression
TBST: Tris-buffered saline with Tween-20

II. Explanations of Terms

Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Addressable: Something that is capable of being reliably and consistently located and identified, as in an addressable location on an array.

Array: An arrangement of molecules, particularly biological macromolecules (such as polypeptides or nucleic acids) or cell or tissue samples, in addressable locations on or in a substrate. The array may be regular (arranged in uniform rows and columns, for instance) or irregular. The number of addressable locations on the array can vary, for example from a few (such as three) to more than 50, 100, 200, 500, 1000, 10,000, or more. A "microarray" is an array that is miniaturized so as to require or be aided by microscopic examination for evaluation or analysis.

Within an array, each arrayed sample (feature) is addressable, in that its location can be reliably and consistently determined within the at least two dimensions of the array. Thus, in ordered arrays the location of each sample is assigned to the sample at the time when it is applied to the array, and a key may be provided in order to correlate each location with the appropriate target or feature position. Often, ordered arrays are arranged in a symmetrical grid pattern, but samples could be arranged in other patterns (e.g., in radially distributed lines, spiral lines, or ordered clusters). Addressable arrays usually are computer readable, in that a computer can be programmed to correlate a particular address on the array with information about the sample at that position (e.g., hybridization or binding data, including for instance signal intensity). In some examples of computer readable formats, the individual features in the array are arranged regularly, for instance in a Cartesian grid pattern, which can be correlated to address information by a computer.

The sample application location on an array (the "feature") may assume many different shapes. Thus, though the term "spot" is used herein, it refers generally to a localized placement of molecules or cells, and is not limited to a round or substantially round region. For instance, substantially square regions of application can be used with arrays encompassed herein, as can be regions that are, for example substantially rectangular, triangular, oval, irregular, or another shape.

In certain example arrays, one or more features will occur on the array a plurality of times (e.g., twice or more), for instance to provide internal controls.

Binding or interaction: An association between two substances or molecules. For instance, arrays are used to detect binding or other interaction of a labeled molecule (termed a "probe" herein) with an immobilized target molecule in the array. A probe "binds" to a target molecule in a feature on an array if, after incubation of the probe (usually in solution or suspension) with or on the array (or a slice of the array) for a period of time (usually 5 minutes or more, for instance 10 minutes, 20 minutes, 30 minutes, 60 minutes, 90 minutes, 120 minutes or more), a detectable amount of the probe associates with a feature of the array to such an extent that it is not removed by being washed with a relatively low stringency buffer. Appropriate buffers for washing CryoArrays may be adapted based on the constituents of the features of the array, and for instance may be those used in washing nucleic acid hybridization systems (e g., higher salt (such as 3×SSC or higher), room temperature washes), protein interaction systems (e.g., 100 mM KCl), and so forth. Washing can be carried out, for instance, at room temperature, but other temperatures (either higher or lower) can also be used.

Probes will bind target molecules to different extents, and the term "bind" encompasses both relatively weak and relatively strong interactions. Thus, some binding will persist after the array is washed in a way that is appropriate to remove the probe molecule, or a portion thereof, such as the portion that is not specifically associated with a molecule or component of the array. For instance in a lower salt buffer (such as about 0.5 to about 1.5×SSC), 55–65° C. washes can be used for nucleic acid probes, or a higher salt buffer (e.g., 500 mM or 1000 mM KCl, TBST) for protein probes, and so forth.

Where the probe and target molecules are nucleic acids, binding of the probe to a target can be discussed in terms of the specific complementarity between the probe and the target nucleic acid. Where either the probe or the target is a protein, specificity of binding and binding affinity can be discussed.

The term "binding characteristics of an array for a particular probe" refers to the specific binding pattern that forms between the probe and the array after excess (unbound or not specifically bound) probe is washed away. This pattern (which may contain no positive signals, some or all positive signals, and will likely have signals of differing relative intensity) conveys information about the binding affinity of that probe for molecules within the spots of the array, and can be de-coded by reference to the key of the array (which lists the addresses of the spots on the array surface). The relative intensity of the binding signals from individual features in many embodiments is indicative of the relative level in a particular feature on the array of the target that binds to or interacts with the probe. Quantification of the binding pattern of an array/probe combination (under particular probing conditions) can be carried out using any of several existing techniques, including scanning the signals into a computer for calculation of relative density of each spot.

cDNA: A DNA molecule lacking internal, non-coding segments (introns) and regulatory sequences which determine transcription. cDNA molecules may be synthesized in the laboratory by reverse transcription from messenger RNA extracted from cells.

Comparative Genomic Hybridization (CGH): A technique of differential labeling of test DNA and normal reference DNA, which are hybridized simultaneously to chromosome spreads, as described in Kallioniemi et al., *Science* 258:818–821, 1992, which is incorporated by reference.

CryoArray: An array of samples, such as biological samples, placed into a block of substrate (such as embedding compound) at addressable locations, which loaded block is then sliced (sectioned) to produce a plurality of sequential cryosections, each containing a portion of the samples in the block. The samples "freeze" into the block of substrate, such that the loaded block can be sectioned and will maintain the portions of sample in addressable locations that correlate to the locations of the samples in the loaded block. Examples of CryoArrays include protein CryoArrays (in which the samples contain one or more known or unknown proteins), and nucleic acid CryoArrays (in which the samples contain one or more known or unknown nucleic acids). Additional non-limiting examples of CryoArrays are discussed herein.

In some embodiments, CryoArrays are constructed as a block containing substantially columnar samples contained in wells in the block. Once one or more samples are loaded into wells in the cryoblock, it (the block) can be sliced (sectioned) to provide a plurality of identical or substantially identical individual arrays. The individual arrays can be used for parallel analysis of the same set of array features, for instance with different probes or under different conditions on different slices from the same array block. In order to maintain substantially similar feature size and placement on sequential cryosections from a single cryoblock, the wells in the block may be formed perpendicular to the surface from which sections are removed. However other configurations of the array are possible. For example, the columns may be non-parallel to each other, but will vary in a predictable relationship to one another, such that the position at which each column intersects a section can be predicted. Similarly, the cryosections optionally can be made at an angle other than parallel to the face of the array block.

The shape of the CryoArray substrate itself is essentially immaterial, though it is usually substantially flat on at least one side and examples are rectangular or square in general shape. For instance, CryoArray blocks that are cylindrical are envisioned, wherein the elongated axis of the sample wells runs approximately parallel to the axis of the cylinder.

DNA (deoxyribonucleic acid): DNA is a long chain polymer that contains the genetic material of most living organisms (the genes of some viruses are made of ribonucleic acid (RNA)). The repeating units in DNA polymers are four different nucleotides, each of which includes one of the four bases (adenine, guanine, cytosine, and thymine) bound to a deoxyribose sugar to which a phosphate group is attached. Triplets of nucleotides (referred to as codons) code for each amino acid in a polypeptide, or for a stop signal. The term "codon" is also used for the corresponding (and complementary) sequences of three nucleotides in the mRNA into which the DNA sequence is transcribed.

EST (Expressed Sequence Tag): A partial DNA or cDNA sequence, typically of between 200 and 2000 sequential nucleotides, obtained from a genomic or cDNA library, prepared from a selected cell, cell type, tissue or tissue type, organ or organism, which corresponds to an mRNA of a gene found in that library. An EST is generally a DNA molecule sequenced from and shorter than the cDNA from which it is obtained.

Freezing: The term "freezing" and "frozen" as they are used herein refers to the solidification of a liquid or fluid sample, to a point of solidity (rigidity) sufficient that it can be sectioned or sliced. Freezing usually occurs at a temperature at or below the freezing temperature of water, but where the sample contains constituents other than water, the "freezing" (solidification) point may be substantially different from 0° C.

Fluorophore: A chemical compound, which when excited by exposure to a particular wavelength of light, emits light (i.e., fluoresces), for example at a different wavelength. Fluorophores can be described in terms of their emission profile, or "color." Green fluorophores, for example Cy3, FITC, and Oregon Green, are characterized by their emission at wavelengths generally in the range of 515–540λ. Red fluorophores, for example Texas Red, Cy5 and tetramethylrhodamine, are characterized by their emission at wavelengths generally in the range of 590–690λ.

Examples of specific fluorophores are provided in U.S. Pat. No. 5,866,366 to Nazarenko et al., and include for instance: 4-acetamido-4'-isothiocyanatostilbene-2,2'-disulfonic acid, acridine and derivatives such as acridine and acridine isothiocyanate, 5-(2'-aminoethyl) aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Brilliant Yellow, coumarin and derivatives such as coumarin, 7-amino-4-methylcoumarin (AMC, Coumarin 120), 7-amino-4-trifluoromethylcouluarin (Coumaran 151); cyanosine; 4',6-diaminidino-2-phenylindole (DAPI); 5',5"-dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulfonic acid; 5-[dimethylamino]naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate;

ethidium; fluorescein and derivatives such as 5-carboxyfluorescein (FAM), 5-(4,6-dichlorotriazin-2-yl) aminofluorescein (DTAF), 2'7'-dimethoxy-4'5'-dichloro-6-carboxyfluorescein (JOE), fluorescein, fluorescein isothiocyanate (FITC), and QFITC (XRITC); fluorescamine; IR144; IR1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron .RTM. Brilliant Red 3B-A); rhodamine and derivatives such as 6-carboxy-X-rhodamine (ROX), 6-carboxyrhodamine (R6G), lissamine rhodamine B sulfonyl chloride, rhodamine (Rhod), rhodamine B, rhodamine 123, rhodamine X isothiocyanate, sulforhodamine B, sulforhodamine 101 and sulfonyl chloride derivative of sulforhodamine 101 (Texas Red); N,N,N',N'-tetramethyl-6-carboxyrhodamine (TAMRA); tetramethyl rhodamine; tetramethyl rhodamine isothiocyanate (TRITC); riboflavin; rosolic acid and terbium chelate derivatives.

Other suitable fluorophores include GFP (green fluorescent protein) and variants and derivatives thereof, Lissamine™, diethylaminocoumarin, fluorescein chlorotriazinyl, naphthofluorescein, 4,7-dichlororhodamine and xanthene and derivatives thereof. Other fluorophores known to those skilled in the art may also be used in the methods described herein.

High-throughput Genomics: Application of genomic or genetic data or analysis techniques that use (micro)arrays or other genomic technologies to rapidly identify large numbers of genes or proteins, or distinguish their structure, expression or function from normal or abnormal cells or tissues.

Human Cells: Cells obtained from a member of the species *Homo sapiens*. The cells can be obtained from any source, for example peripheral blood, urine, saliva, tissue biopsy, surgical specimen, amniocentesis samples and autopsy material. From these cells, genomic DNA, cDNA, mRNA, RNA, and/or protein can be isolated.

Hybridization: Nucleic acid molecules that are complementary to each other hybridize by hydrogen bonding, which includes Watson-Crick, Hoogsteen or reversed Hoogsteen hydrogen bonding between complementary nucleotide units. For example, adenine and thymine are complementary nucleobases that pair through formation of hydrogen bonds. "Complementary" refers to sequence complementarity between two nucleotide units. For example, if a nucleotide unit at a certain position of an oligonucleotide is capable of hydrogen bonding with a nucleotide unit at the same position of a DNA or RNA molecule, then the oligonucleotides are complementary to each other at that position. The oligonucleotide and the DNA or RNA are complementary to each other when a sufficient number of corresponding positions in each molecule are occupied by nucleotide units which can hydrogen bond with each other.

"Specifically hybridizable" and "complementary" are terms that indicate a sufficient degree of complementarity such that stable and specific binding occurs between the oligonucleotide and the DNA or RNA target. An oligonucleotide need not be 100% complementary to its target DNA sequence to be specifically hybridizable. An oligonucleotide is specifically hybridizable when binding of the oligonucleotide to the target DNA or RNA molecule interferes with the normal function of the target DNA or RNA, and there is a sufficient degree of complementarity to avoid non-specific binding of the oligonucleotide to non-target sequences under conditions in which specific binding is desired, for example under physiological conditions in the case of in vivo assays, or under conditions in which the assays are performed.

Hybridization conditions resulting in particular degrees of stringency will vary depending upon the nature of the hybridization method of choice and the composition and length of the hybridizing DNA used. Generally, the temperature of hybridization and the ionic strength (especially the $Na^+$ concentration) of the hybridization buffer will determine the stringency of hybridization. Calculations regarding hybridization conditions required for attaining particular degrees of stringency are discussed by Sambrook et al., chapters 9 and 11 (*Molecular Cloning: A Laboratory Manual*, Cold Spring Harbor, New York, 1989), incorporated herein by reference.

Stringent conditions may be defined as those under which DNA molecules with more than 25%, 15%, 10%, 6% or 2% sequence variation (also termed "mismatch") will not hybridize. Stringent conditions are sequence dependent and are different in different circumstances. Longer sequences hybridize specifically at higher temperatures. Generally, stringent conditions are selected to be about 5° C. lower than the thermal melting point $T_m$ for the specific sequence at a defined ionic strength and pH. An example of stringent conditions is a salt concentration of at least about 0.01 to 1.0 M Na+ ion concentration (or other salts) at pH 7.0 to 8.3 and a temperature of at least about 30° C. for short probes (e.g. 10 to 50 nucleotides). Stringent conditions can also be achieved with the addition of destabilizing agents such as formamide. For example, conditions of 5×SSPE (750 mM NaCl, 50 mM sodium phosphate, 5 mM EDTA, pH 7.4) and a temperature of 25–30° C. are suitable for allele-specific probe hybridizations.

In those embodiments wherein one or more of the samples on the array comprise whole cells, in situ hybridization approaches may be appropriate. Such methods are well known to those of ordinary skill in the relevant fields. In addition, in such embodiments methods can be employed to lyse the cells prior to probing the array, to facilitate access of the probe molecule(s) to the constituents of the cells in the samples.

Isolated: An "isolated" biological component (such as a nucleic acid molecule, protein or organelle) has been substantially separated or purified away from other biological components in the cell of the organism in which the component naturally occurs, i.e., other chromosomal and extra-chromosomal DNA and RNA, proteins and organelles, or from other components in the reaction mixture used to generate the molecule (if it is synthesized in vitro). Nucleic acids and proteins that have been "isolated" include nucleic acids and proteins purified by standard purification methods. The term embraces nucleic acids and proteins prepared by recombinant expression in a host cell as well as chemically synthesized molecules.

Label: Detectable marker or reporter molecules, which can be attached to nucleic acids, for example probe molecules. Typical labels include fluorophores, radioactive isotopes, ligands, chemiluminescent agents, metal sols and colloids, and enzymes. Methods for labeling and guidance in the choice of labels useful for various purposes are discussed, e.g., in Sambrook et al., in *Molecular Cloning: A Laboratory Manual*, Cold Spring Harbor Laboratory Press (1989) and Ausubel et al., in *Current Protocols in Molecular Biology*, Greene Publishing Associates and Wiley-Intersciences (1987).

Malignant: A term describing cells that have the properties of anaplasia, invasion and metastasis.

Neoplasia: Abnormal growth of cells, including benign and malignant neoplasms.

Nucleic acid: A deoxyribonucleotide or ribonucleotide polymer in either single or double stranded form, and unless otherwise limited, encompassing known analogues of natural nucleotides that hybridize to nucleic acids in a manner similar to naturally-occurring nucleotides.

Nucleic acid array: An arrangement of nucleic acids (such as DNA or RNA) in assigned or addressable, or determinable locations on a matrix, such as that found in cDNA or CGH arrays, or in examples of the herein described CryoArrays.

Nucleic acid molecules representing genes: Any nucleic acid, for example DNA, cDNA or RNA, of any length suitable for use as a probe that is informative about the corresponding gene.

Oligonucleotide: A linear single-stranded polynucleotide sequence ranging in length from 2 to about 1,000,000 bases, for example a polynucleotide (such as DNA or RNA) which is at least 6 nucleotides, for example at least 15, 50, 100, 200, 1,000, 10,000 or even 1,000,000 nucleotides long. Oligonucleotides are often synthetic but also can be produced from naturally occurring polynucleotides.

An oligonucleotide analog refers to moieties that function similarly to oligonucleotides but have non-naturally occurring portions. For example, oligonucleotide analogs can contain non-naturally occurring or altered sugar moieties or inter-sugar linkages, such as a phosphorothioate oligodeoxynucleotide. Functional analogs of naturally occurring polynucleotides can bind to RNA or DNA, and include peptide nucleic acid (PNA) molecules. Such analog molecules may also bind to or interact with polypeptides or proteins.

Oligopeptide: A linear peptide molecule of about 100 or fewer amino acid residues.

Plant Cells: Cells obtained from any member of the *Plantae* Kingdom, a category which includes, for example, trees, flowering and non flowering plants, grasses, and *Arabidopsis*. The cells can be obtained from any part of the plant, for example roots, leaves, stems, or any flower part. From these cells, nucleic acid and/or protein can be isolated.

Peptide Nucleic Acid (PNA): An oligonucleotide analog with a backbone comprised of monomers coupled by amide (peptide) bonds, such as amino acid monomers joined by peptide bonds.

Pooled Arrays: In certain CryoArrays, referred to as pooled arrays, at least one particular address on the array is occupied by a pooled mixture of more than one substantially pure target molecule, e.g., one or more pure polypeptide. All of the addresses on the array may contains pools of molecules, or only some of the addresses, depending on the use of the array. For instance, in some circumstances it may be desirable to array a target polypeptide associated with one or more non-target polypeptides, for instance a stabilizing polypeptide or linker molecule. In addition, the native conformation of certain binding sites on proteins can only be assayed for probe binding when the target polypeptide is associated with other molecules, for instance when the target polypeptide natively exists as one subunit of a multimeric complex, or when the protein occurs in complex with a nucleic acid molecule.

Pooled arrays include those in which one or more of the addresses contains a defined multimeric complex. In the case of such an array, it is envisioned that different probe molecules may bind to different molecules (e.g., polypeptides) within the complex that is the "target."

Although the identity of each probe in the pooled mixture at a specific address is usually known, the individual probes in the pool are not technically "separately addressable." The binding signal from a pooled address is the binding signal of the set of different (but mixed or associated) molecules occupying that address. In general, an address is considered to display binding of a probe molecule if at least one molecule occupying the address binds to or interacts with the probe molecule.

Arraying pooled samples is also a powerful tool in high-throughput technologies for increasing the information that is yielded each time the array is assayed.

Probe: A molecule that may bind to or interact with one or more targets (e.g., biological macromolecules or cells). A probe, as the term is used herein, can be any molecule that is used to challenge ("probe," "assay," "interrogate" or "screen") a CryoArray in order to determine the binding, activity, or interaction characteristics of the arrayed target(s) with that probe molecule.

In specific embodiments, probes may be from different and varied molecular classes. Such classes are, for, instance, nucleic acids (such as single or double stranded DNA or RNA), oligo- or polypeptides (such as proteins, for instance antibodies, protein fragments including domains or subdomains, and mutants or variants of naturally occurring proteins), or various types of other potential polypeptide-binding molecules. Such other molecules are referred to herein generally as ligands (such as drugs, toxins, venoms, hormones, co-factors, substrates or reaction products of enzymatic reactions or analogs thereof, transition state analogs, minerals, salts, and so forth).

The term probe, as used herein, also encompasses substrates and/or assays systems used to assess the activity of a target within a feature of the array. Thus, it is contemplated that CryoArray sections can be assayed for the activity of a protein in one or more features using a probe that is a substrate of that protein (which substrate may contain a label, as discussed herein), or a probe that is a reporter system that interacts with the target protein to produce a detectable signal. Similarly, in some embodiments where cells (e.g., bacterial or yeast cells) form the features, some probes are assay systems upon which the cells (or constituents within the cells) perform a biological reaction, which reaction produces a detectable signal. For instance, if the cells in the array have been transformed with a construct that may express a gene from a reporter system (e.g., the β-gal system or another such research system), then the components of the reporter system would form a probe useful in assaying the array to detect expression.

Usually, a probe molecule for use in probing a CryoArray is detectable or produces a detectable product. Probes can be detectable based on their inherent characteristics (e.g., immunogenicity, color, fluorescence) or can be rendered detectable by being labeled with an independently detectable tag or label. The tag may be any recognizable feature that is, for example, microscopically distinguishable in shape, size, color, optical density, etc.; differently absorbing or emitting of light; chemically reactive; magnetically or electronically encoded; or in some other way detectable. Specific examples of tags are fluorescent or luminescent molecules that are attached to the probe, or radioactive monomers or molecules that can be added during or after synthesis of the probe molecule. Other tags may be immunogenic sequences (such as epitope tags) or molecules of known binding pairs (such as members of the strept/avidin:biotin system). Additional tags and detection systems are known to those of skill in the art, and can be used in the disclosed methods.

Though in many embodiments of the invention a single type of probe molecule (for instance one protein) at a time will be used to assay the array, in some embodiments, mixtures of probes will be used, for instance mixtures of two proteins or two nucleic acid molecules. Such co-applied probes may be labeled with different tags, such that they can be simultaneously detected as different signals (e.g., two fluorophores that emit at different wavelengths, or two gold particles of different sizes).

In specific embodiments, one of these co-applied probes will be a control probe (or probe standard), which is designed to hybridize to a known and expected sequence in one or more of the spots on the array.

In some provided examples of CryoArrays and methods of probing them, the probe is a heterogeneous mixture, for instance a heterogeneous mixture of nucleic acid molecules or proteins. For instance, a probe may be a pool of cDNA or other nucleic acid molecules, likely labeled. This type of probe can be used to assay a nucleic acid-based CryoArray that contains individual nucleic acid molecules much as a traditional cDNA array is assayed; signal at a specific locus indicates that the pooled probe (which may be reflective of expression levels in a cell sample) contains nucleic acids corresponding to the target molecule at that locus. Similarly, a pool of proteins (for instance, a protein preparation from a cell sample) can be used as a probe to assay a CryoArray that contains known proteins (e.g., known antibodies or other proteins), and signal at a locus on the array interpreted as an indication that the pool contains one or more proteins that interact with the target in that locus (e.g., contains an antigen the target antibody at that locus has affinity for).

In specific embodiments, probes may be single or double stranded nucleic acid, but will often be single-stranded DNA or RNA. In specific embodiments, the probe will be single, positive-strand nucleic acid, particularly in those embodiments wherein the mixtures of nucleic acids immobilized on the array include cDNA molecules.

Probe standard: A probe molecule for use as a control in analyzing an array. Positive probe standards include any probes that are known to interact with at least one of the targets of the array. Negative probe standards include any probes that are known not to specifically interact with at least one target of the array. Probe standards that may be used in any one system include molecules of the same class as the test probe that will be used to assay the array. For instance, if the array will be used to examine the interaction of a protein with polypeptides in the array, the probe standard can be a protein or oligo-or polypeptide.

In some examples of CryoArrays, for instance certain arrays that contain mixtures of nucleic acids in the features, a control probe sequence can be designed to hybridize with a so-called "housekeeping" gene. For instance, the housekeeping gene is one which is known or suspected to maintain a relatively constant expression level (or at least known to be expressed) in a plurality of cells, tissues, or conditions. Many of such "housekeeping" genes are well known; specific examples include histones, β-actin, or ribosomal subunits (either mRNA encoding for ribosomal proteins or rRNAs). Housekeeping genes can be specific for the cell type being assayed, or the species or Kingdom from which sample used in the array features has been produced. For instance, ribulose bis-phosphate carboxylase oxygenase (RuBisCO), an enzyme involved in plant metabolism, may provide useful positive control probes for use with arrays if the nucleic acid mixtures arrayed have been derived from plant cells or tissues. Likewise, probes from the RuBisCO sequence (or any other plant-specific sequence) could provide good negative controls for gene profiling array spots that include animal-derived samples.

Additional controls for specific embodiments are discussed below.

In some instances, as in certain of the kits that are provided herein, a probe standard will be supplied that is unlabeled. Such unlabeled probe standards can be used in a labeling reaction as a standard for comparing labeling efficiency of the test probe that is being studied. In some embodiments, labeled probe standards will be provided in the kits.

Probing: As used herein, the term "probing" refers to incubating an array with a probe molecule (usually in solution) in order to determine whether the probe molecule will bind to, hybridize or otherwise interact with molecules immobilized on the array. Synonyms include "interrogating," "challenging," "screening" and "assaying" an array. Thus, a CryoArray is said to be "probed" or "assayed" or "challenged" when it is incubated with a probe molecule (such as a labeled or otherwise detectable polypeptide, nucleic acid molecule, or ligand, or a positive, single-stranded and detectable nucleic acid molecule that corresponds to a gene of interest).

Protein/Polypeptide: A biological molecule expressed by a gene or other encoding nucleic acid, and comprised of amino acids. More generally, a polypeptide is any linear chain of amino acids, usually about 50 or more amino acid residues in length, regardless of post-translational modification (e.g., glycosylation or phosphorylation).

Examples of CryoArrays include a plurality of polypeptide samples (targets) placed at addressable locations within an array substrate (e.g., a block of OCT embedding material). The polypeptide at each location can be referred to as a target polypeptide, or target polypeptide sample.

In certain embodiments, polypeptides are deposited into the array in a substantially native configuration, such that at least a portion of the individual polypeptides within the locus is in a native configuration. Such native configuration-polypeptides are capable of binding to or interacting with molecules in solution that are applied to the surface of the array section in a manner that approximates natural intra-or intermolecular interactions. Thus, binding of a molecule in solution (for instance, a probe) to a target polypeptide immobilized in an array will be indicative of the likelihood of such interactions in the natural situation (ie., within a cell). In some embodiments the polypeptides in features of a CryoArray retain function and therefore can be assayed for an activity.

One of the benefits of the provided system of protein analysis using CryoArrays is maintaining samples, particularly protein samples, at or below freezing during the preparation of the cryoblock and cryosections.

Protein purification: Polypeptides for use in the present invention can be purified by any of the means known in the art. See, e.g., Guide to Protein Purification, ed. Deutscher, Meth. Enzymol. 185, Academic Press, San Diego, 1990; and Scopes, Protein Purification: Principles and Practice, Springer Verlag, New York, 1982.

Proteomics: Global, whole-cell analysis of gene expression at the protein level, yielding a protein profile for a given cell or tissue. The comparison of two protein profiles (proteomes) from cells that have been differently treated (or that are otherwise different, for instance genetically) provides information on the effects the treatment or condition (or other difference) has on protein expression and modification. Subproteomics is analysis of the protein profile of a portion a cell, for instance of an organelle or a protein complex. Thus, a mitochondrial proteome is the profile of the protein expression content of a mitochondrion under certain conditions. Proteomic analysis is increasingly be performed using peptide and protein arrays; such arrays are reviewed in Emili and Cagney (*Nat. Biotech.* 18:393–397, 2000).

Purified: The term purified does not require absolute purity; rather, it is intended as a relative term. Thus, for example, a purified nucleic acid preparation is one in which the specified nucleic acid is more enriched than the nucleic acid is in its generative environment, for instance within a cell or in a biochemical reaction chamber. A preparation of substantially pure nucleic acid may be purified such that the desired nucleic acid represents at least 50% of the total nucleic acid content of the preparation. In certain embodiments, a substantially pure nucleic acid will represent at least 60%, at least 70%, at least 80%, at least 85%, at least 90%, or at least 95% or more of the total nucleic acid content of the preparation. Similarly, a preparation of substantially pure protein may be purified such that the desired protein represents at least 50% of the total protein content of the preparation. In certain embodiments, a substantially pure protein will represent at least 60%, at least 70%, at least 80%, at least 85%, at least 90%, or at least 95% or more of the total protein content of the preparation.

Recombinant: A recombinant nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

RNA: A typically linear polymer of ribonucleic acid monomers, linked by phosphodiester bonds. Naturally occurring RNA molecules fall into three classes, messenger (mRNA, which encode proteins), ribosomal (rRNA, components of ribosomes), and transfer (tRNA, molecules responsible for transferring amino acid monomers to the ribosome during protein synthesis). Total RNA refers to a heterogeneous mixture of all three types of RNA molecules.

Serial Analysis of Gene Expression (SAGE): A method that uses short sequence tags to allow the quantitative and simultaneous analysis of a large number of transcripts in tissue, as described in Velculescu et al., *Science* 270:484–487, 1995, which is incorporated by reference.

Stripping: Bound probe molecules can be stripped from an array, for instance a protein CryoArray, in order to use the same array for another probe interaction analysis (e.g., to determine the level of a different protein in the arrayed samples, particularly where the arrayed samples contain mixtures of proteins). Any process that will remove substantially all of the first probe molecule from the array, without also significantly removing the immobilized nucleic acid mixtures of the array, can be used. By way of example only, one method for stripping a protein array is by washing it in stripping buffer (e.g., 1 M $(NH_4)_2SO_4$ and 1 M urea), for instance at room temperature for about 30–60 minutes. By way of example only, one method for stripping an array containing nucleic acids is by boiling it in stripping buffer (e.g., very low or no salt with 0.1% SDS), for instance for about an hour or more. Usually, the stripped array will be equilibrated, for instance in a low stringency wash buffer, prior to incubation with another probe molecule.

Subject: Living, multicellular vertebrate organisms, a category that includes both human and veterinary subjects, for example, mammals, birds, and primates.

Target: As used herein, individual molecules, cells, or mixtures that are placed in to a CryoArray are referred to as targets. Targets on a single array can be derived from several to thousands of different samples, such as cell or tissue types (more generally, from a plurality of specimens). In certain embodiments of the arrays and methods described herein, the target feature on the array contains a heterogeneous mixture of molecules that proportionately reflects the levels of the starting (source) material from which the molecules are derived; such arrays can be used to comparatively examine the level of constituents in an array feature. Thus, in specific examples, the features of the array contain mRNA or mRNA-derived molecules (e.g., aRNA, cRNA or cDNA) that are present in proportionate amounts to the nucleic acids they represent in the starting sample (e.g., tissue) from which the mRNA was extracted to generate the feature. Similarly, some arrays will include features that contain heterogeneous mixtures of proteins that reflect the levels (e.g., proportionate levels) of those proteins in a starting material, such as a tissue sample.

In general, a target on the array is discrete, in that signals from that target can be distinguished from signals of neighboring targets, either by the naked eye (macroarrays) or by scanning or reading by a piece of equipment or with the assistance of a microscope (microarrays).

Tumor: A neoplasm that may be either malignant or non-malignant. "Tumors of the same tissue type" refers to primary tumors originating in a particular organ (such as breast, prostate, bladder or lung). Tumors of the same tissue type may be divided into tumors of different sub-types (a classic example being bronchogenic carcinomas (lung tumors), which can be an adenocarcinoma, small cell, squamous cell, or large cell tumor).

Unless otherwise explained, all technical and scientific terms used herein have the same meaning as commonly understood by one of ordinary skill in the art to which this invention belongs. The singular terms "a," "an," and "the" include plural references unless context clearly indicates otherwise, and the term "comprising" means "including." It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

III. Overview of Several Embodiments

In one embodiment, this disclosure provides methods of making a CryoArray, which methods involve providing a substrate (e.g., a gel, such as an embedding compound) having a plurality of sample wells, placing one or more liquid samples in one or more of the sample wells (usually one sample per well), then freezing the samples in the sample wells to produce a loaded array. This loaded array can then be section into a plurality of cryosections such that the samples are at addressable locations in the cryosections.

In specific examples of such methods, the substrate is maintained at or below freezing while the samples are placed in the sample wells and frozen. In some of the provided methods, the samples are bonded to the substrate when the samples are frozen.

In various examples of the provided methods of making CryoArrays, the samples contain an acellular biological substance (for instance, a protein, a nucleic acid, a lipid, a carbohydrate, or a mixture of two or more of these substances), a suspension of cells (for instance, animal cells, plant cells, protist cells, bacterial cells, or fungal cells, or mixtures thereof), a suspension of viruses, a biological fluid (e.g., blood, a blood product, urine, sweat, tears, saliva, spit, an amniocentesis sample, semen, or mucous), or an environmental sample.

In some provided embodiments, the sample wells are elongated and substantially parallel to each other, and they may be oriented substantially transverse to opposing surfaces of the substrate.

Also provided are CryoArrays (either loaded with sample or "blank" blocks, containing sample wells but no samples or an incomplete sample set) made using the described methods, and individual cryosections cut from such CryoArrays.

Other embodiments provide methods of parallel analysis of samples, such as biological samples (e.g., a protein, a mixture of proteins, a nucleic acid, a mixture of nucleic acids, a cell, a virus, or a biological fluid). Examples of these methods involve obtaining a plurality of (biological) samples, and placing each in an addressable location in a recipient array (for instance, a blank CryoArray) to produce a loaded array. In specific embodiments, particularly where it is beneficial to preserve the biological structure of function of a constituent of one or more sample on the array, the recipient array is kept at or below freezing while the samples are being placed in the array. Sections can be cut (for instance, using a microtome or other device) from loaded arrays (arrays into which samples have been placed). In some of the provided methods, sections are cut from the arrays in a manner such that each section contains a plurality of portions of the samples placed in the array, which each maintain their assigned location. Sections from the provided CryoArrays can be used to perform one or more biological analyses of samples in the arrays.

In some of the provided methods, the biological samples are placed into recipient array as liquids (for instance, suspensions), and frozen after being placed in the array.

As provided herein, a recipient array substrate may include an embedding compound that is solid at 0° C. In some embodiments, recipient array contains a plurality of wells to receive the biological samples. Examples of such wells have a substantially circular cross section having a diameter of less than about 2 mm.

In specific provided examples of methods for parallel analysis of samples, more that one biological analysis (for instance, an immunological binding assay, protein binding assay, activity assay, amplification reaction, or nucleic acid hybridization) is performed on more than one section of a loaded array. The results of such analyses can be compared for the more than one biological analyses in corresponding assigned locations of different sections form the array to determine if there is a correlation between the results of the different biological analyses at different assigned locations.

In various embodiments, the results of the different biological analyses performed on sections of a CryoArray are used to evaluate a reagent for disease diagnosis or treatment (e.g., evaluating a reagent selected from the group of antibodies, genetic probes, and antisense molecules, or a reagent selected from the group of biological inhibitors, biological enhancers, or other biological modulators); identify a prognostic marker for cancer; identify a prognostic marker for a non-cancerous disease; select targets for drug development; prioritize targets for drug development; assess or select therapy for a subject; and/or find a biochemical target for medical therapy.

In specific examples of such analyses, identifying a prognostic marker for cancer or identifying a prognostic marker for a non-cancerous disease involves selecting a marker associated with a poor clinical outcome.

In still other examples of such analyses, selecting therapy for the subject involves selecting an antineoplastic therapy that is associated with a particular biological analysis outcome.

Also provided are methods of analyzing a CryoArray, which methods involve providing a plurality of elongated biological samples at addressable locations in a block of embedding substrate, such that when the block is frozen and cut into predetermined array sections, a two dimensional array of portions of the biological samples is presented at a surface of each section, with each portion of the biological samples at an addressable location in the array sections, and wherein each biological sample in the block has a third dimension so that when sequential sections of the block are cut, the biological samples maintain a predetermined relationship in the array sections; and exposing a plurality of the array sections to a probe that interacts with one or more of the biological samples of the array, to identify those biological samples that share or differ in a biological property.

In some examples of these methods, the common biological property is a molecular characteristic, such as a presence or absence, or altered level of expression, of a protein or gene, alteration of copy number, structure or function of a gene, genetic locus, chromosomal region or chromosome. In some embodiments, the common biological property is correlated with at least one other characteristic of the samples, for instance clinical information (one or more of clinical course, tumor stage, oncogene status, and age of the subject from whom each sample was taken) about a subject from whom each sample was taken.

These and additional embodiments are described more fully below.

IV. CryoArrays

It has surprisingly been found that samples (such as purified or mixed protein, nucleic acid, virus, cell, or biological fluid samples) can be analyzed in parallel on arrays that are prepared at low temperatures, referred to herein as CryoArrays. In a disclosed embodiment, CryoArrays are constructed as a block (for instance, of embedding compound) containing elongated, substantially columnar samples (see FIG. 1A), which block is sliced (sectioned; FIG. 1B) across the elongated axis of the samples to provide a plurality of identical or substantially identical individual arrays (cryosections), each cryosection containing a portion of each of the samples. Production of many substantially identical CryoArray sections (in some embodiments, 100–800 sections per block, depending on the thickness of the cryoblock and the thickness of the sections) is simple, relatively inexpensive, and requires only a small volume of sample (usually about 2–6 $\mu$l/well, depending on the size of the cryoblock and the cross-sectional area of the sample wells). For instance, from a 12 mm cryoblock, 800 10 $\mu$M sections could be cut (equivalent to 8 mm of the block thickness).

The ability to make multiple cryosections from one cryoblock enables parallel analysis of many corresponding, for example substantially identical, arrays using minute amounts of samples, some of which may be precious or otherwise in short supply. Individual arrays can be used for parallel analysis of the same array feature set, for instance with different probes or under different conditions. In addition, the process is biomolecule compatible, particularly protein compatible, because samples are kept frozen or near freezing during production of the cryoblock. CryoArrays are useful for screening small samples of rare or precious biological fluids or tissues for biomarkers, and for rapid screening of monoclonal antibodies.

CryoArrays, and examples of methods for their preparation and use, are described in more detail below, beginning with a detailed description of several of the accompanying drawings.

Figure 1B:
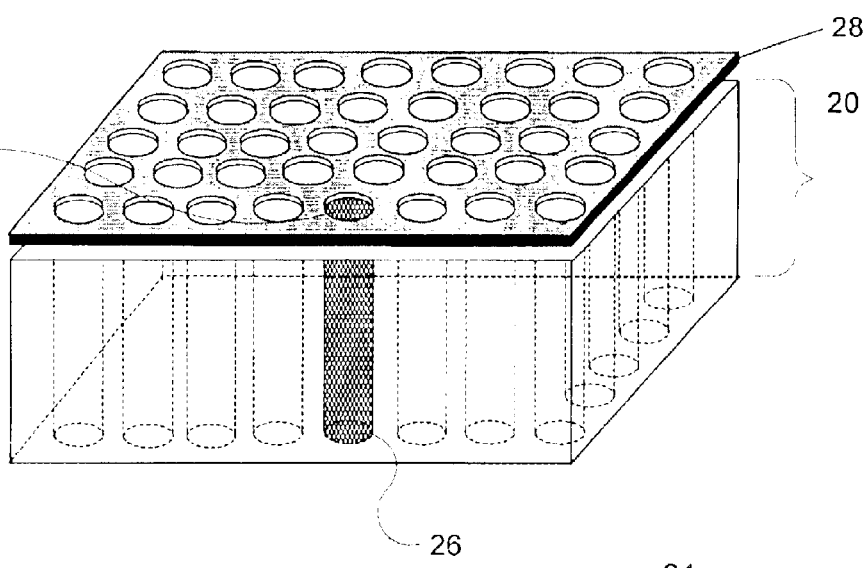
In FIG. 1B, one section (cryosection) has been removed from the top of the cryoblock and is shown suspended slightly above the remainder of the block.

An outline representation of a prepared CryoArray block 20 is shown in FIG. 1. In the illustrated embodiment (FIG. 1A), block 20 is a regular parallelepiped having at least one face 22. Contained within block 20 are a plurality of sample wells 24, of which forty are shown in the illustrated embodiment in FIG. 1. Sample wells 24 are generally elongated and substantially columnar in shape, substantially perpendicular to face 22, and extend into but not necessarily all the way through block 20. Though the illustrated sample wells 24 have a circular cross section, this is not essential; other cross sectional profiles are contemplated. Similarly, though sample wells 24 are illustrated as being substantially the same diameter throughout their entire length, and as having a flat interior bottom surface, neither of these features is essential. Sample wells 24 with for instance sloped or ridged interior surfaces, and/or sloped, domed, or cone-shaped interior bottom surfaces are also envisioned; other shapes could also be used.

Once the sample (illustrated by the shading in one representative loaded sample well 26) has been injected into one or more of sample wells 24, thus producing a loaded CryoArray block, one or more sections 28 are removed from face 22. Sections 28 are removed using, for instance, a cryostat or microtome device, and generally are relatively thin, usually less than a millimeter thick, ie., on the order of 2–50 $\mu M$ thick. Being removed from face 22 of block 20, sections 28 are sliced essentially perpendicularly to the elongated axis of sample wells 24, and thus sections 28 contain cross-sectional portions 30 of loaded samples, such as representative sample in loaded sample well 26. Each section 28 can then be used, directly or after transfer to a transfer substrate surface, for analysis of sample.

Figure 2:
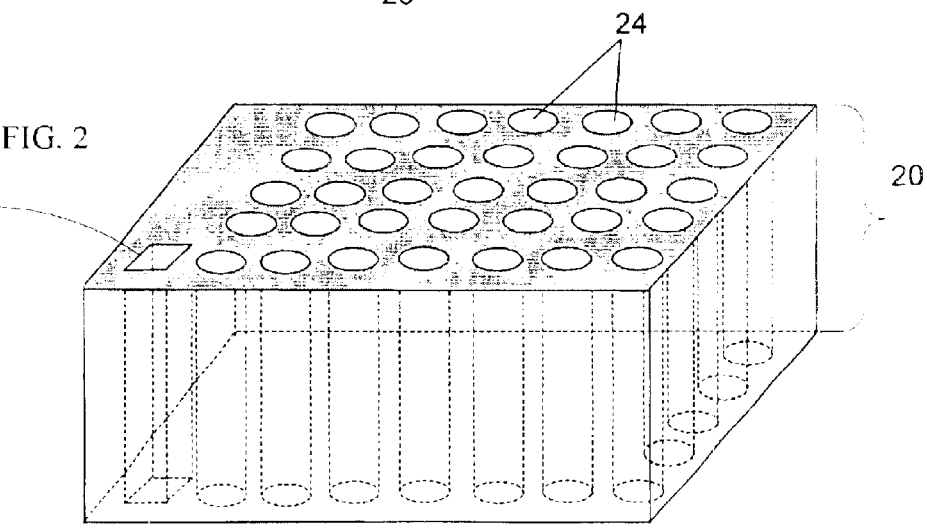
FIG. 2 Shows a schematic drawing of another example CryoArray block, wherein an orientation well has been included. In this particular example, the orientation well is both slightly separated from and of a different shape than the remainder of the wells in the block.

In certain embodiments, as illustrated in FIG. 2, the CryoArray block 20 includes one or more orientation wells 32, which can be used to reliably orient individual cryosections from the array. In the illustrated embodiment, orientation well 32 is both separated somewhat from sample wells 24, and has a different cross-sectional profile than does a sample well 24. Neither separation nor a different profile is a required feature in all embodiments having an orientation well 32, as long addressable locations of the array can be determined, for instance if orientation well 32 can in some way be distinguished from sample wells 24 in the cryosections produced from such blocks.

FIG. 3 is a series of schematic views showing the sectioning of a loaded CryoArray, and the removal of three individual sections from the array block for use in three different analyses. A representative loaded cryoblock 34 is illustrated in oblique view in FIG. 3A, showing a plurality (twenty-five in this embodiment) of loaded sample wells 26. Sample wells 26 are arranged in loaded cryoblock 34 in a regular array format, wherein each sample well 26 has a round cross sectional profile that is of a consistent width 36, and where each sample well 26 is separated from neighboring sample wells 26 by a defined and constant distance 38. FIG. 3B illustrates the removal of a single cryosection 28 from loaded cryoblock 34. The removal of three sequential cryosections (28a, 28b, and 28c) from loaded cryoblock 34 is shown in frontal view FIG. 3C. Each of cryosections 28, once removed from loaded cryoblock 28, can be probed for the presence, absence, or quantity of a target molecule in the samples contained on that cryosection. This is illustrated by the separation of cryosections 28a, 28b, and 28c onto different pieces of transfer substrate (40) in FIG. 3D, FIG. 3E, and FIG. 3F, respectively.

Figure 4:
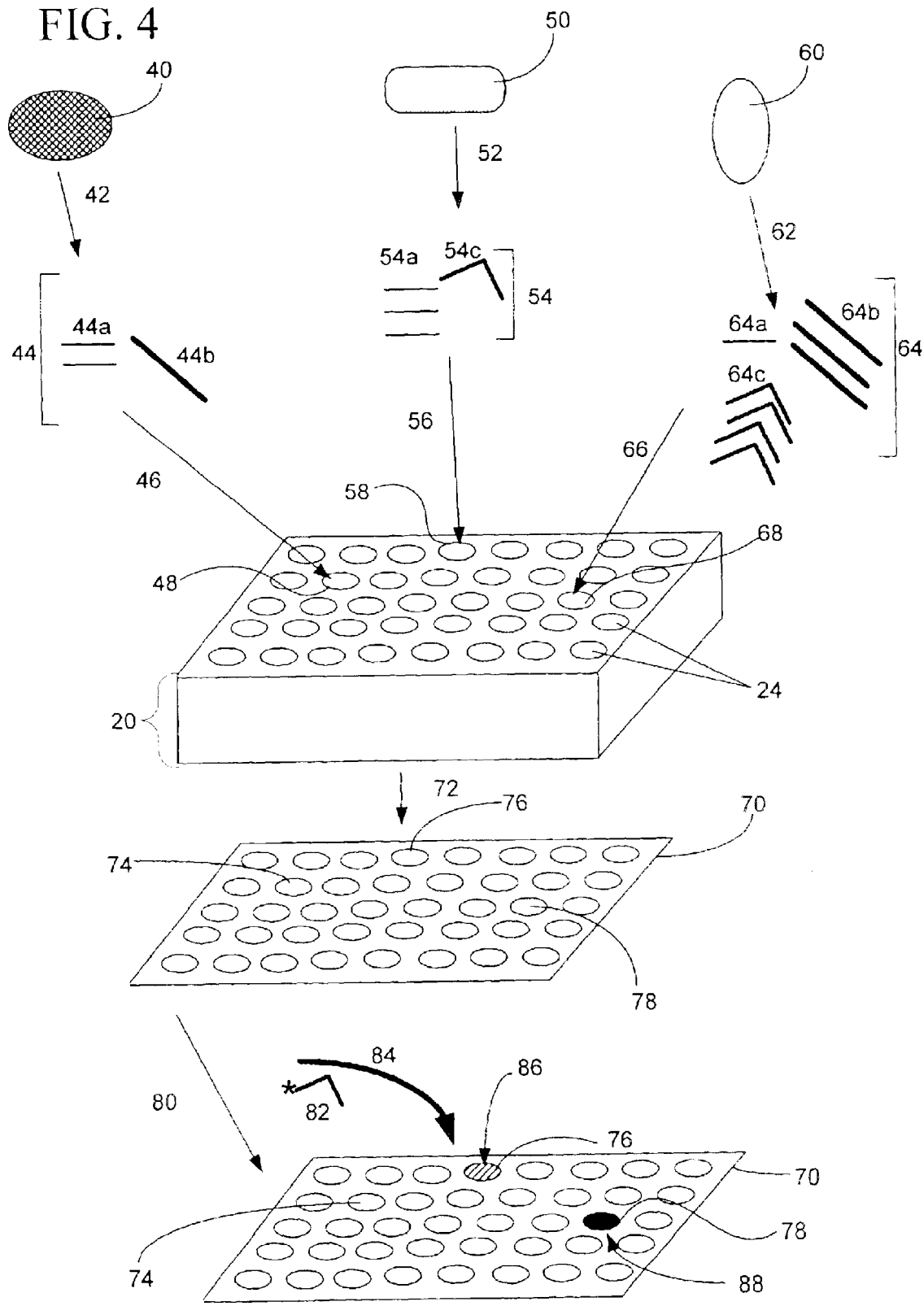
FIG. 4 is a schematic outline showing construction and probing (with a labeled (*) probe) of a CryoArray wherein two signal intensities are detected.

One use of a CryoArray is illustrated in FIG. 4, which provides schematic views of the construction and probing (with a labeled (*) probe) of a CryoArray wherein two signal intensities are detected on a resultant cryosection. In the illustrated embodiment, a first source sample 40 (e.g., a cell, tissue, fluid sample) is subjected to a process 42, such as extraction process, resulting in a prepared sample 44. Prepared sample 44 contains two types of molecule (e.g., two different nucleic acid sequences, two different proteins, a nucleic acid and a protein, etc.), types a and b, referred to within sample 44 as 44a and 44b. Prepared sample 44 is placed, usually by injection (46) into a sample well 24 within a prepared cryoblock 20, generating loaded sample well 48. In many embodiments, cryoblock 20 is maintained at a low temperature (e.g., at or below freezing), such that when samples (such as prepared sample 44) are injected into a sample well 24, the sample freezes and bonds onto the inner surface of the sample well 24.

This process is repeated for additional source samples 50 and 60, which also are subjected to a process (52 and 62, respectively) that produces prepared samples 54 and 64, respectively. In addition to molecule types a and b, found in prepared sample 44, prepared samples 54 and 64 each contain molecules of type c; thus, prepared sample 54 contains molecules of type a (54a) and type c (54c), while prepared sample 64 contains molecules of all three types (64a, 64b, and 64c). Prepared samples 54 and 64 are loaded (by process 56 and 66) into sample wells 24 in cryoblock 20, to produce additional loaded sample wells 58 and 68, respectively. Additional samples (not shown) can be prepared and loaded into additional sample wells 24.

When all of the desired samples have been loaded into sample wells 24 of cryoblock 20, one (or more) sections (such as illustrated cryosection 70) are removed (process 72) from face 22 of cryoblock 20 using, for instance, a microtome or cryostat device (not shown). Because cryosections (e.g., cryosection 70) are removed from face 22, they are sliced transversely across the elongate access of the sample wells 24, and the resultant cryosection (70) contains a cross sectional portion of each sample placed into sample wells 24. In the illustrated examples, loaded sample 48, when sliced transversely to produce cryosection 70, produces cross sectional portion 74, contained within the slice of embedding material that cryosection 70 is made of. Similarly, transverse sectioning of loaded sample 58 yields cross sectional sample portion 76; and transverse sectioning of loaded sample 68 produces cross sectional sample portion 78. Sequential sections taken from the same loaded cryoblock produce additional cryosections, each containing a cross sectional sample portion from each of the loaded samples. Each of the cross sectional sample portions contained with individual cryosections contains a portion of the sample, and therefore a portion of the molecules contained within the sample.

In order to probe a cryosection (such as illustrated cryosection 70), the cryosection is usually removed from the sectioning apparatus (not shown) by adhering the section to a surface that is adhesive on one side (e.g., tape, such as Scotch Tape), which adhesive can adhere to the cold surface of the cryosection without substantially distorting the two dimensional arrangement of sample portions within the section. In addition to facilitating removal of the cryosection from the sectioning apparatus, the adhesive surface provides support for the cryosection, particularly in embodiments where a probing reaction is carried out directly on the cryosection (without subsequently transferring the section to a transfer substrate surface). Optionally, a cryosection 70 can be transferred to a transfer substrate surface (not shown), such as a nitrocellulose membrane or membrane patch deposited on a slide (e.g., as with FAST™ slides).

One embodiment of a probing reaction carried out on a cryosection is shown in FIG. 4. Cryosection 70 is subjected to a probing process 80, during which a probe molecule 82 (in the illustrated embodiment, a labeled probe molecule 82, where the label is indicated with an asterisk) is applied (84) to the cryosection 70 (or a replica of the cryosection, as described herein). In the illustrated embodiment, probe 82 is a molecule that binds specifically to molecules of type c, and thus probe 82 binds to molecules contained within at least cross sectional sample portions 76 (corresponding to source sample 50) and 78 (corresponding to source sample 60).

In certain embodiments, the intensity of the probe binding signals is also measured. Detection of different signal intensities is also schematically depicted in FIG. 4. By virtue of the label on probe 82, those cross sectional sample portions that contain molecules to which probe 82 binds give off a signal. Thus, cross sectional sample portion 76 gives off a signal 86 after labeled probe 82 is bound thereto, which signal has a certain intensity that, in the illustrated embodiment is proportional to the amount of molecules of type c are contained in that sample portion. Similarly, cross sectional sample portion 78 gives off signal 88 after labeled probe 82 is bound thereto, which signal is also proportional to the amount of molecules of type c contained within that sample portion. Reading this probing reaction of cryosection 70, it thus is apparent that prepared sample 54 and 64 both contained molecules of type c (which bind labeled probe 82), and that 44 does not contain molecules of type c. It is also apparent that prepared sample 64 contains substantially more molecules of type c than does prepared sample 54, based on the relative intensities of probe signals 88 and 86, respectively.

In one specific embodiment (illustrated in FIG. 5) a CryoArray is formed from a solid block of frozen histologic embedding compound (OCT; 12×19×12 mm) containing a 5×5 matrix of 600 µm diameter wells spaced 2 mm apart. In this embodiment, the wells were formed using needles placed upright into the embedding material before it was frozen, and removed after the block was fully frozen. Optionally one or more orientation wells (illustrated in FIG. 5B) may be included in the block, to permit reliable orientation of the cryosections; these orientation wells can be filled with a colored solution or another detectable and identifiable substance or molecule. Optionally, one or more control samples may be included in the array, to serve as positive (or negative) controls for probing the individual cryosections.

The sample wells in the frozen block are filled with biological samples (FIG. 5C), of which several types are described herein, which freeze and bond to the OCT block. Next, sections (e.g., 10 µm sections) are cut from the face of the cryoblock on a cryostat. In some embodiments, the cryosections are transferred to nitrocellulose-coated slides using a tape-transfer or other system that preserves the geometry of the samples in the array; one cryosection, on a piece of tape, is shown in FIG. 5D. In this particular embodiment, each spot on the cryosection contains 3 nl of sample.

Sequential sections taken from a single cryoblock can be tested, for instance for protein expression by immunohistochemistry, or protein function by direct activity assay. In other embodiments, nucleic acids can be detected and/or quantified.

The reproducibility and linearity of the CryoArray system has been confirmed using a block filled with different concentrations of fluoro-labeled-IgG, as described in Example 4. The fluorescent signal was reproducible (coefficient of variation 3.6–10.1%), and linear over a 16-fold concentration range ($R^2$=0.94).

The ability of the CryoArray system to detect both recombinant and native proteins was tested using modified immunohistochemical methods, as described in Example 5. Recombinant human prostate specific antigen (PSA, 0.1 ng/µl) could be detected using an anti-PSA antibody with a detection limit of 0.3 pg/spot.

The analyses to which CryoArrays can be applied are myriad, and the following list is provided in order to illustrate rather than limit these uses. It is currently contemplated that CryoArrays can be used as illustrated in the following non-limiting examples:

Protein-Based CryoArrays

Load CryoArray with purified and identified individual proteins, probe using serum or purified antibody from a subject (e.g., to detect or quantify infection or exposure to disease organism);

Load CryoArray with purified proteins or mixed protein preparation, detect and quantify with known antibodies (to quantitate amount of target material in the samples);

Load CryoArray with purified individual or mixed protein, detect or quantify a post-translational characteristic of the proteins (e.g., phosphorylation);

Load CryoArray with individual uncharacterized antibodies (e.g., from newly generated potential monoclones), detect with pure protein (to identify good clones);

Load CryoArray with purified, known antibodies, detect or quantify with mixed proteins (e.g., protein preparation from a cell or tissue sample, a biological fluid sample, a food or environmental sample, and so forth);

Load CryoArray with pure protein or protein mixtures, detect or quantify secondary partner binding (to identify or characterize protein-protein interactions);

Load CryoArray with protein mixtures (e.g., from a cell or other sample), detect or quantify with known antibody(s);

Load CryoArray with protein mixtures (e.g., from a cell or other sample), detect or quantify with an activity assay;

Nucleic Acid-Based CryoArrays

Load CryoArray with nucleic acid mixtures (e.g., from a cell or other sample), detect or quantify with pure nucleic acid (e.g, to study gene expression or gene amplification, to identify a cell or strain);

Load CryoArray with individual identified oligonucleotides or cDNAs, detect or quantify using labeled cDNA mixture (e.g., from a cell or tissue, as in traditional cDNA microarrays);

Load CryoArray with purified individual unknown nucleic acid (e.g., from potential plasmid clones), detect with pure nucleic acid (to identify a desired sequence);

Load CryoArray with mixture of nucleic acids (e.g., a genomic preparation from a cell sample), detect with an identifier nucleic acid sequence (e.g., a ribosomal RNA or other strain/cell-specific sequence, to identify strains/cells)

Cell-Based CryoArrays

Load CryoArray with cells, detect or quantify with antibody (e.g., to identify cells or cell types, or quantify protein expression levels);

Load CryoArray with cells, detect or quantify with a secondary binding partner (e.g., a cell surface binding receptor);

Load CryoArray with cells, detect or quantify with nucleic acid (e.g., to identify cells or cell types, for instance using a ribosomal RNA probe);

Load CryoArray with cells, detect or quantify with nucleic acid (e.g., to identify transformed cells);

Load CryoArray with cells, detect or quantify with activity assay (e.g., to identify transformed cells expressing a marker, to detect cells of a certain natural genotype, etc.);

Load CryoArray with human embryonic stem cells, detect with antibody or activity assay;

Load CryoArray with cells from LCM, detect or quantify with antibody;

Load CryoArray with cells from LCM, detect or quantify with nucleic acid;

Delivery CryoArrays

Load CryoArray with potentially invasive/pathogenic organisms (e.g., viruses, bacteria or fungi), implant into a research animal (to examine invasiveness and pathogenicity);

Load CryoArray with tumor cells (or potentially tumorous cells), implant into a research animal (to examine invasiveness and metastatic potential);

Virus CryoArrays

Load CryoArray with virus samples, detect with protein (e.g., antibody);

Load CryoArray with phage display library, detect with antibodies to desired display components;

Load CryoArray with viruses, detect with nucleic acid;

Sample-Based CryoArrays

Load CryoArray with biological fluid samples, detect biomarkers (e.g., cancer biomarkers, disease biomarkers, etc.);

Load CryoArray with biological fluid samples, detect with antibody;

Load CryoArray with biological fluid samples, detect activity of an enzyme;

Load CryoArray with biological fluid samples, detect virus/infectious agent (e.g., by in situ hybridization or in situ RT/PCR).

Described below are certain characteristics of several different CryoArray embodiments and related methods. The embodiments and examples given are meant in no way to limit the invention.

A. CryoArray Substrate

CryoArrays are formed as a block (referred to as a cryoblock) of a solid embedding medium with wells substantially perpendicular to one surface of the block, into which the samples (features) will be placed. The substrate for the CryoArray is an embedding medium that is sufficiently rigid ("frozen") at least at the temperature at which the block is prepared that it can be sectioned to provide individual cryosections for analysis (e.g., sectioned using a cryostat). Rigidity is a relative term, and in this context refers to sufficient rigidity to maintain samples within the array in substantially the same position in cryosections as they were in the cryoblock, so that individual features remain reliably addressable.

In general, the embedding medium is such that the samples can be bound to it, in order to secure the sample into the well and maintain its placement when the cryoblock is sectioned. Thus, the substrate of the cryoblock may be different for different samples, and either the solution in which the sample is suspended or the substance of the cryoblock can be adjusted in minor ways to ensure that such binding occurs. For some embodiments, optimal binding of the sample to the block substrate is achieved by bringing the osmolarity or osmolality of the liquid sample into relative parity with the osmolarity or osmolality of the block. In some embodiments, a gelling agent (such as a gelatin, agarose, acrylamide, or other gelling agent) is added to the samples to stabilize their binding to the block when they are frozen.

In certain embodiments, it is preferred that the embedding substrate is essentially inert regarding the probing assays that will be carried on cryosections produced from that substrate. Thus, for instance when the probe will be arrayed with a fluorescent system, generally cryoblock substrates that have inherent fluorescence should be avoided.

One specific example of a particularly appropriate embedding material is OCT embedding compound (available from a number of sources, including CryoGel OCT, available from Instrumedics Inc., Hackensack, N.J.). Additional cryoblock substrates for certain embodiments include gelatin (for instance, as found in Jell-O™), pudding, agarose, polyacrylamide, wax (particularly waxes that have appropriate wetting properties so that a CryoBlock constructed from such wax would be both sectionable and able to bond to the sample), and other cross-linked or matrix-forming substrates, including other poly-saccharide gels or matrixes.

B. CryoArray Format

CryoArrays may vary significantly in their format and structure, both of which may be influenced by the intended functionality of the CryoArray. The disclosed array systems are amenable to use in either a macroarray or a microarray format, or a combination thereof. Such arrays can include, for example, at least 10, 25, 50, 100, 150, 200, 500, 1000, or 5000 or more array elements (also referred to as features). In the case of macro-format CryoArrays, detection of bound or interacting probe on the array does not require sophisticated equipment (e.g., a microscope), though quantification may be assisted by automated scanning and/or quantification techniques and equipment.

Macro-format arrays can be of any size, but typically will be greater than a square centimeter. Macroarrays are generally used when the number of array elements is relatively small, on the order of tens to hundreds of samples, however macroarrays with a larger number of array elements can be used on large substrates. Spot arrangement on the macroarray is such that individual spots can be distinguished from each other when the sample is read. In some embodiments, the diameter of the spot is about equal to the spacing between individual dots, though this is not necessary.

Sample locations on macroarrays are of a size large enough to permit their detection without the assistance of a microscope or other sophisticated enlargement equipment. Thus, features may be as small as about 0.1 mm across, with a separation of about the same distance, and can be larger. Larger features on macroarrays, for example, may be about 0.5, 0.6, 0.7, 0.8, 0.9, 1, 2, 3, 5, 7, or 10 mm across. Even larger features may be larger than 10 mm (1 cm) across, in certain specific embodiments. The array size will in general be correlated the size of the individual target locations in the array, in that larger "spots" will usually be found on larger arrays, while smaller spots may be found on smaller arrays. This correlation is not necessary, though.

In microarray-format CryoArrays, a common feature is the relatively small size of the target array, for example an area of about a squared centimeter (1 cm$^2$) or less. A squared centimeter (for example, a square of dimensions 1 cm by 1 cm) is large enough to contain over 2,500 individual target spots, if each spot has a diameter of 0.1 mm and spots are separated by 0.1 mm from each other. Features on a micro-CryoArray will generally be no larger than about 1 mm by 1 mm. The smallest possible diameter of a feature well on a CryoArray may be limited by the viscosity of the fluid the sample is suspended in, and it's freeze-rate. If the diameter of the sample well is too small, or the sample too viscous or too rapidly freezes, the sample will not fill the entire well within the Cryoblock. Gaps in the column of sample may cause individual cryosections from the cryoblock to lack sample, and are therefore to be avoided.

The amount of target that is applied to each address of an array will be largely dependent on the array format used. The volume of the individual wells within the cryoblock are a function of the diameter (more precisely area) of the feature and the depth of the well/thickness of the cryoblock. Thus, a larger spot (having a diameter) or a thicker cryoblock will generally accept or require a greater amount of target molecule than a smaller spot (or the well within a thinner cryoblock).

Characteristics of the target (e.g., the length of a biomolecule, its primary and secondary structure, its binding characteristics in relation to the probe, etc.) will in some instances influence how much of each target is applied to an array, or at what concentration/density it is applied within a well. Optimal amounts of target for application to an array can be empirically determined, for instance by applying varying amounts of the target to an array, producing cryosections from the array, and probing a cryosection with a probe known to interact with at least one target mixture molecule. In this manner, it is possible to empirically determine a range of target amounts that will produce interpretable results with any collection of desired targets.

C. Formation of Sample Wells

Sample-receiving wells in CryoArrays can be produced by any method that places elongated, substantially columnar wells (sample receiving receptacles) into the block substrate. In some embodiments, this involves placing a plurality of pin-like intrusions into the block substrate before it is frozen, then removing the pins to leave a plurality of wells in the block. Alternatively, wells can be drilled or punched into a frozen block of embedding medium. In some embodiments, the wells have a bottom, in that there are not holes that pass through the entire thickness of the cryoblock.

Figure 5A:
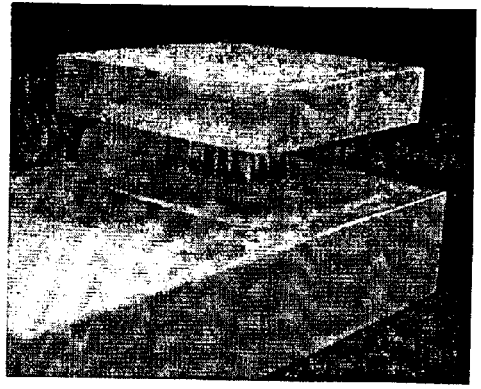
FIG. 5A shows an aluminum 12×19×12 mm mold filled with OCT embedding compound, with a 5×5 array of needles positioned above the cryoblock.
Figure 5B:
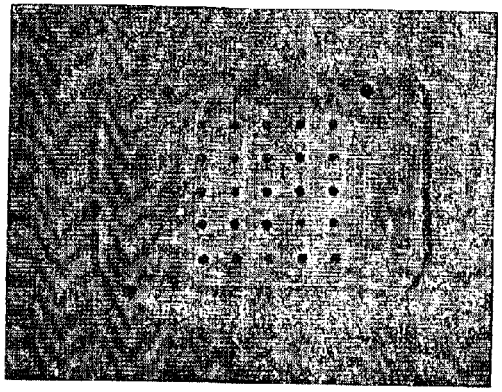
FIG. 5B shows a CryoArray block with sample wells, after the needle array has been removed.
Figure 5C:
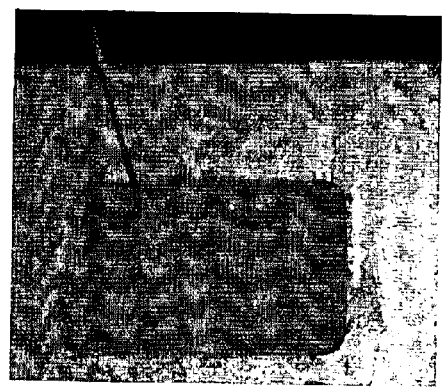
FIG. 5C shows a CryoArray block being filled with a gelatin-based sample.
Figure 5D:
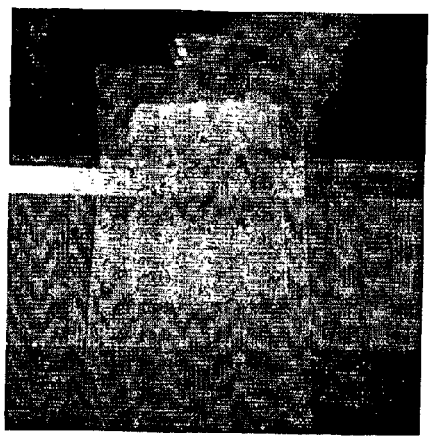
FIG. 5D shows a cryosection of a CryoArray, cut with a cryostat and transferred using a tape transfer system to preserve the geometry of the array.

Optionally one or more orientation wells (as illustrated in FIG. 5B) may be included in the block, to permit reliable orientation of the cryosections; these orientation wells can be filled with a colored solution or another detectable and identifiable substance or molecule. Optionally, one or more control samples may be included in the array, to serve as positive (or negative) controls for probing the individual cryosections. Control samples can be placed in any of the sample wells within the array, though it is particularly envisioned that control samples would be placed along one row (or column) of sample wells, or at a corner, or in some other recognizable pattern within the array.

Orientation wells, used to reliably identify the orientation of cryosections removed from a cryoblock, are in some way distinguishable from sample wells on the same block, and can for instance be of a different size or shape than sample wells, though this is not essential. Similarly, it is not essential that all the sample wells in an array block be the same size or shape, though this facilitates direct comparison of quantified signals. In some embodiments, orientation wells are placed away from, or out of the ordered pattern of, the matrix of sample wells.

D. Protein-Based CryoArrays

CryoArrays provide several advantages over prior technologies and methods used for analysis of molecule-molecule interactions, for instance protein-molecule interactions (e.g., protein-protein, protein-nucleic acid, protein-ligand, protein-antibody). Additionally, because CryoArrays are generated under very cold conditions, as well as non-denaturing conditions, they provide a simple system for detecting native interactions between molecules (e.g., polypeptides) contained in the individual features and probe molecules, as well as functional assaying of proteins on the arrays in some embodiments.

Targets on examples of protein-based CryoArrays may comprise mixtures of proteins or peptides (e.g., that have been isolated from a cell or tissue, or an environmental sample), or individual purified oligopeptides, polypeptides, proteins, or fragments of these molecules. Oligopeptides, containing between about 8 and about 50 linked amino acids, can be synthesized readily by chemical methods.

Longer polypeptides or proteins, on the other hand, contain up to several thousand amino acid residues, and are not as easily synthesized through in vitro chemical methods. Instead, polypeptides and proteins for use in CryoArrays are usually expressed using one of several well-known cellular expression systems. Alternatively, individual proteins can be isolated from their native environment, for instance from tissue samples or environmental samples, or from expression chambers in the case of engineered expressed polypeptides. After extraction and appropriate purification, the polypeptide can be injected or otherwise placed into the array using any of a variety of techniques.

In one embodiment, the CryoArray is loaded with purified and identified individual proteins, for instance known antigens from disease organisms, proteins from disease organisms, or proteins that are characteristic of a condition (e.g., cancer), and the resultant cryosections are probed using antibody from a subject (e.g., a serum preparation) in order to detect or quantify infection or exposure to a disease organism, or the presence of a disease or condition.

In another embodiment, the CryoArray is loaded with purified individual or mixed protein preparation, and array sections are probed for the presence (or absence, or quantity) of a post-translational modification of the proteins (e.g., phosphorylation).

Other embodiments of CryoArrays are loaded with individual uncharacterized or partially characterized antibodies (e.g., from newly generated potential monoclones). The production of a desired antibody by individual clones can be detected by probing cryosections from such an array with pure protein or antigen that was used to generate the clones.

In other embodiments, CryoArrays are loaded with purified, known antibodies, for instance a set of antibodies to antigens of disease organisms or cancers, and the resultant cryosections probed with a mixed protein preparation (e g., protein preparation from a cell or tissue sample, a biological fluid sample, a food or environmental sample, and so forth) in order to determine if any of the antigens recognized by the arrayed antibodies are present in the mixed sample.

Protein-based CryoArrays can also be used to detect or quantify secondary partner binding and to identify or characterize protein-protein interactions, by loading the array with pure proteins or protein mixtures and probing with potential binding partners.

Protein CryoArrays can also be generated in which the samples comprise proteins mixtures (e.g., crude protein preparations from cells or other samples), and the presence (and/or quantity) of a specific antigen in each of the samples can be detected by probing with a known antibody.

It is also contemplated that protein based CryoArrays can be used to assay the activity of proteins, for instance by loading the array with protein mixtures (e.g., from cell or other samples), then detect or quantify the protein of interest using an activity assay for that protein.

It is beneficial in certain embodiments to apply a known amount of each target polypeptide on the array. In particular embodiments, an essentially equal amount of each target polypeptide is applied to each array location. Quantification and equivalent application of the targets permits comparison of probe binding affinity between the different targets. Measurements of the amount of specific target proteins (e.g., before they are loaded into a CryoArray) may be carried out using any of many techniques well known in the art. These include quantitative immunoblot analysis, enzyme activity assays (where appropriate), and commercially available protein quantification kits (e.g., Bio-Rad protein assay systems), which latter method determines the concentration of protein in a sample regardless of biological characteristics of the specific protein being measured.

Many other techniques could be used to measure the amount of a target protein present in a sample. For instance, the amount of target protein in a sample could be measured using a quantitative enzyme-linked immunosorbant assay ('ELISA') as described by Aboagye-Mathiesen et al. (*Placenta* 18:155–61, 1997).

1. Choice of Purified Polypeptide Targets

The target(s) of interest are selected according to a wide variety of methods. For example, certain targets of interest are well known and included in public databases such as GenBank or a similar commercial database. Other targets are identified from journal articles, or from other investigations using high throughput technologies (e.g., cDNA microarrays or Gene Chips), or with other techniques. In certain embodiments, the sequences of arrayed target polypeptides can be provided via an ASCII text file, for instance to assist data storage, sorting, and comparison.

Any polypeptides can serve as targets for use in the subject arrays. For instance, an array (or set of arrays) could be assembled that reflects every protein encoded for by the genome of an organism. Alternatively, arrays can be designed that contain a specific family of proteins. Such families can be defined in various ways, including proteins that act in a specific cellular process (e.g., transcription-related proteins), proteins that are in a linked biochemical pathway (e.g., proteins involved in the respiratory pathway), proteins known to be involved in diseases, etc. Arrays can also be produced that include proteins of a specific type (e.g., DNA polymerases) from various different species. Arrays of the oligopeptides or polypeptides encoded for by ESTs also can be created, and are useful for identifying, characterizing, or analyzing the function of individual EST-linked genes and the proteins they encode.

In essence, any combination or grouping of individual polypeptides can be assembled together one or a set of CryoArrays for simultaneous analysis of interaction with one or more probes of interest.

By way of example, it is believe that there are approximately 40,000 different genes in the human genome, and it is expected that all of them will be known within the next few years. There are many more proteins making up the proteome of an organism, due to alternative splicing of messages, post translational modifications, and so forth. With the provision of every gene in the human genome, proteins encoded for by each human gene can be arrayed on one or a collection of CryoArrays, such that the entire human complement of proteins can be screened for probe interactions. Arrays can also be arranged that contain collections of proteins encoded on a single human chromosome, such that a collection of 23 CryoArrays would represent the entire (or substantially the entire) human genome.

Genome-wide or chromosome-specific polypeptide arrays or array sets are not limited to the human genome. Any species for which the genome is known or becomes known could be arrayed on one or a collection of arrays according to this invention. Such non-human genomes include those from disease organisms (e.g., viruses, bacteria, parasites, etc.), research organisms (*Drosophila melanogaster, Caenorhabditis elegans, Xenopus laevis, Arabidopsis, Saccharomyces cerevisiae, Escherichia coli*, etc.), and so forth.

Polypeptide CryoArrays also may be used to perform further analysis on genes and targets discovered from, for example, high-throughput genomics, such as DNA sequencing, DNA microarrays, or SAGE (Serial Analysis of Gene Expression) (Velculescu et al., *Science* 270:484–487, 1995). Polypeptide CryoArrays also may be used to evaluate reagents for disease or cancer diagnostics, for instance specific antibodies or probes that react with certain polypeptides from infectious organisms or from tissues at different stages of cancer development. This technology can also be used to follow progression of polypeptide changes both in the same and in different cancer types, or in diseases other than cancer. Polypeptide CryoArrays may be used to identify and analyze prognostic markers or markers that predict therapy outcome for various diseases or abnormal conditions, such as cancers. Arrays compiled from the proteins of hundreds of cancers derived from patients with known disease outcomes permit binding or association assays to be performed on those arrays, to determine important prognostic markers, or markers predicting therapy outcome, which are associated with polypeptide binding characteristics.

Polypeptide CryoArrays may also be used to help assess the ability of certain drugs or potential drugs to interact with target polypeptides, or the ability of such molecules to block the interaction of other probes with arrayed polypeptides.

CryoArrays can be used to investigate receptor specificity of different types of known and suspected receptor molecules. Examples of receptors that can be investigated for probe-specific binding by arrays include but are not limited to microorganism receptors (for instance, those found in fungi, protozoa, and bacteria, especially bacterial strains that are resistant to antibiotics); hormone receptors (including those involved in diabetes, growth regulation, vasoregulation, and so forth); and opiate receptors (involved in biological responses, for instance to addictive drugs).

Also envisioned are arrays that are custom produced for a researcher, with an arrayed collection of polypeptides tailored to a specific research project, research system, etc.

Not in any way intending to be limited to the list below, the following is a list of the types of collections of polypeptides that can be arrayed on a CryoArray: all or substantially all the proteins encoded for by the genome of an organism; all or substantially all the proteins encoded for by a chromosome of an organism; proteins expressed in a cell during a particular growth phase or environmental condition; proteins expressed in a cell under a particular abnormal state (such as cancer, disease, or infection); proteins expressed in cells at various times during the progression of a disease or condition (e.g., during progression of a tumor, or development of a chronic disease such as Alheizmers); proteins expressed in a particular cell type; proteins from a particular protein family (e.g., DNA polymerases, cell surface proteins, transmembrane proteins or fragments [such as soluble fragments] thereof, oncogene proteins, tumor suppressor proteins, and so forth); proteins that show sequence homology to each other; proteins that share secondary structural characteristics; proteins that associate to form multimeric complexes (e.g., the subunits of a ribosome or a membrane ATPase); viral epitopes; domains of proteins; proteins from different species; antibodies (e.g., antibodies to a set of known proteins, or a collection of uncharacterized or partially characterized antibodies); and collections of fragments of any of these protein collections.

2. Production of Substantially Pure Target Polypeptides

Polypeptides for use as targets on purified polypeptide CryoArrays can be produced by any technique that yields native protein. These techniques in general include expression from engineered DNA constructs, extraction from native samples (e.g., clinical samples), or de novo synthesis of oligopeptide or polypeptide fragments.

Expression of the target polypeptides can be carried out using well-known techniques. For instance, partial or full-length cDNA sequences, which encode the protein of interest as a target on the array, may be ligated into bacterial expression vectors. Methods for expressing large amounts of protein from a cloned gene introduced into *Escherichia coli* (*E. coli*) may be utilized for the production and purification of intact, native target proteins. Methods and plasmid vectors for producing fusion proteins and intact native proteins in bacteria are described in Sambrook et al. (Sambrook et al., In *Molecular Cloning: A Laboratory Manual*, Ch. 17, CSHL, New York, 1989). Such fusion proteins may be made in large amounts and are easy to purify. Native proteins can be produced in bacteria by placing a strong, regulated promoter and an efficient ribosome-binding site upstream of the cloned gene. If low levels of protein are produced, additional steps may be taken to increase protein production; if high levels of protein are produced, purification is relatively easy. Suitable methods are presented in Sambrook et al. (In *Molecular Cloning: A Laboratory Manual*, CSHL, New York, 1989) and are well known in the art. Often, proteins expressed at high levels are found in insoluble inclusion bodies. Methods for extracting proteins from these aggregates are described by Sambrook et al. (In *Molecular Cloning: A Laboratory Manual*, Ch. 17, CSHL, New York, 1989). Vector systems suitable for the expression of lacZ fusion genes include the pUR series of vectors (Ruther and Muller-Hill, *EMBO J.* 2:1791, 1983), pEX 1–3 (Stanley and Luzio, *EMBO J.* 3:1429, 1984) and pMR100 (Gray et al., *Proc. Natl. Acad. Sci. USA* 79:6598, 1982). Vectors suitable for the production of intact native proteins include pKC30 (Shimatake and Rosenberg, *Nature* 292:128, 1981), pKK177–3 (Amann and Brosius, *Gene* 40:183, 1985) and pET-3 (Studiar and Moffatt, *J. Mol. Biol.* 189:113, 1986).

3. Choice of Mixtures of Polypeptides

Any mixture of proteins can be used to as a sample on a CryoArray. It is particularly contemplated that protein mixtures may be reflective of the levels of proteins in the cells or tissues from which the proteins were isolated. Thus, arrays may include cellular protein preparations from a collection of cancer cells, a collection of cells from different tissues, a collection of cells from different species, and so forth.

As with individual protein CryoArrays, it is beneficial in certain embodiments to apply a known amount of target polypeptide mixtures on the array. Quantification of such mixtures can be carried out essentially as described above for individual protein preparations.

In certain arrays, referred to as pooled arrays, at least one particular address on the array is occupied by a pooled mixture of more than one target polypeptide. All of the addresses on the array may contains pools of polypeptides, or only some of the addresses, depending on the use of the array. For instance, in some circumstances it may be desirable to array a target polypeptide associated with one or more non-target polypeptides, for instance a stabilizing polypeptide or linker molecule. In addition, the native conformation of certain binding sites on proteins can only be assayed for probe binding when the target polypeptide is associated with other molecules, for instance when the target polypeptide natively exists as one subunit of a multimeric complex. Pooled arrays include those on which one or more of the addresses contains a multimeric polypeptide complex. In the case of such an array, it is envisioned that different probe molecules may bind to different polypeptides within the complex of "target" polypeptides.

Although the identity of each target polypeptide in a pooled mixture at a specific address may be known, the individual targets in the pool are not "separately addressable." The binding signal from a pooled address is the binding signal of the set of different (but mixed or associated) polypeptides occupying that address. In general, an address within an array is considered to display binding of a probe molecule if at least one polypeptide (or other target) occupying the address binds to the probe molecule.

Arraying pooled samples is also a powerful tool in high-throughput technologies for increasing the information that is yielded each time the array is assayed. Methods for analyzing signals from arrays containing pooled samples have been described, for instance in U.S. Pat. No. 5,744,305, incorporated herein by reference in its entirety.

4. Production of Mixtures of Polypeptides

Mixtures of polypeptides used as targets in CryoArrays are usually isolated from a source, such as a tissue or cell sample, a reaction mixture (e.g., an in vitro translation system), an environmental sample, and so forth, using a relatively crude purification process. For instance, cellular homogenates can be used a source of a protein mixture that is applied to a CryoArray. General strategies for generating protein preparations can be found, for instance, in Chapter 10 of *Short Protocols in Molecular Biology* (Ausubel et al., eds., Wiley & Son, Inc., 1999; ISBN 0-471-32938-X).

Cell homogenates can be loaded directly onto CryoArrays, or can be mixed with one or more optional additional components, such as protease inhibitors, an extraction buffer containing detergent(s), SDS/Laemmli buffer, and so forth.

In addition to crude protein preparations, it is contemplated that more defined or more highly purified protein preparations can also be applied to CryoArrays. For instance, cells can be fractionated and protein extracted from individual fractions (such as nuclear, plastid, mitochondrial, cell wall, cytoplasm, and so forth). Other fractionation characteristics could be used, such as charge, size, binding to an affinity column (e.g., heparin, a lectin, etc.). A single array (or series of arrays) could contain samples fractionated using different methods, to provide different subsets of components, and could be used to characterize fractionation techniques. Methods for fractionation of different cell types are well known to those of ordinary skill, and specific techniques for fractionation will be chosen based on the cell type beingo investigated, as well as the fraction desired.

E. Nucleic Acid-Based CryoArrays

The provided CryoArray parallel analysis system can be used to examine samples containing nucleic acids, for instance acellular, fluid samples that contain a single nucleic acid species, or samples that contain a mixture of nucleic acids.

By way of example, it is contemplated that in some embodiments mixtures of nucleic acids which have been extracted from cell samples are applied to wells of a CryoArray, and cryosections from the loaded block are probed with a pure, known nucleic acid probe (e.g., an oligonucleotide) to study gene expression or gene amplification. This system could also be used to identify a cell or strain, for instance by using a nucleic acid probe that is specific for a cell of interest (e.g., a cancerous cell, a transformed cell, a pathogenic cell, etc.). Mixtures of nucleic acids may be amplified prior to being placed into the array, for instance by PCR or other in vitro amplification procedures.

Other CryoArray embodiments are loaded with mixtures of nucleic acids (e.g., a genomic preparations from cell samples), and the resultant cryosections are probed using an identifier nucleic acid sequence (e.g., a ribosomal RNA or other strain/cell-specific sequence, to identify strains/cells).

In other embodiments, the CryoArray is loaded with individual identified oligonucleotides or cDNAs, and the resultant cryosections are probed using a labeled cDNA mixture (e.g., from a cell or tissue, which mixture may be reflective of the expression level of individual mRNAs in that cell or tissue); to detect or quantify the individual nucleic acids represented in individual features of the array.

Nucleic acid-based CryoArrays can also be used to confirm transformation of cells, or cloning of individual sequences. For instance, plasmids purified from a collection of potentially transformed microbial cells can be loaded onto a CryoArray in individual wells, and the presence of a specific nucleic acid sequence (e.g., a recombinant fragment being cloned into the plasmid) can be detected using a labeled oligonucleotide probe specific for that target sequence. Similarly, extracts from cells producing virus (e.g., a recombinant viral vector) could be applied to an array, and the presence (or absence) of a desired nucleic acid could be examined by probing with a nucleic acid specific for the desired sequence.

Similarly to the pooled protein arrays discussed above, the individual target nucleic acids in the pool at each feature are not "separately addressable." However, the pool itself is addressable, and a binding signal from a pooled address is interpreted as binding of the probe molecule (e.g., a specific labeled oligonucleotide) with one or more target nucleic acids within the pooled feature.

Specific examples of nucleic acid CryoArrays are referred to as gene profiling Cryoarrays, which function essentially as the reverse of classic cDNA microarray technology. Heterogeneous, mRNA-derived nucleic acid library pools are applied to the cryoblock as test samples, and the pools of nucleic acid are probed with a known oligonucleotide (or protein) probe.

In certain embodiments of nucleic acid-based CryoArrays, the intensity of the probe binding signals (e.g., nucleic acid hybridization signals) is measured. Hybridization intensity can be compared (between different spots on an array, between different molecule probes such as two test probes or between a test probe and a control probe or standard) in order to determine the relative expression level of the target to which the probe binds, for instance in the nucleic acid mixture occupying the address that displays a positive probe signal. Gene expression CryoArrays permit the simultaneous analysis of gene expression in an entire collection of cell/tissue samples represented on the array, and yields a "cell expression" or "tissue expression" profile for that gene. In addition, by labeling two or more different probe sequences with different tags, multiple genes can be profiled simultaneously on the same array. The two (or more) probe sequences can be used to challenge the array either simultaneously or in sequence; using different tags.

Another type of nucleic acid-based CryoArray that is contemplated is an in situ amplification CryoArray, in which pairs of oligonucleotide primers are loaded into the wells of the cryoblock and the cryosection is overlaid (for instance, in a gelling matrix) with a nucleic acid preparation that contains the reagents necessary to carry out an in vitro nucleic acid amplification reaction. A signal is detected at those features in which the oligonucleotide pair can serve as primers in the amplification reaction. This method resembles to some extent methods described in Tillib et al., 292:155–160, 2001 ("Integration of multiple PCR amplifications and DNA mutation analyses by using oligonucleotide microchip") and PCT/US00/30835, but overcomes limitations of those methods by providing multiple copies of each array of oligonucleotides.

F. "Cellular" CryoArrays

In addition to acellular arrays (those that contain a biological component in the samples, but not cells), it is contemplated that the provided CryoArrays can be used with samples that contain whole cells in suspension. Cells in this context refers to any cells, including bacterial, fungal, plant, and animal cells, for instance, mammalian cells, more particularly cells taken from a human subject.

In some embodiments of "cellular" CryoArrays, it is beneficial to break the target cells open before assaying cryosections of the array. This may be true, for instance, when the target molecule that is detected is contained within the cell, for instance is a nucleic acid molecule or a protein component contained within the cytoplasm of the cell.

In certain embodiments, CryoArrays are loaded with cells in suspension, and the presence or absence (or quantity) of cells of a certain type is detected using an antibody as a probe (e.g., such CryoArrays can be used to identify cells or cell types, or quantify protein expression levels). Alternatively, cells can be detected using a secondary binding partner of a protein known or suspected to be present on the cells (e.g., a cell surface binding receptor).

In other embodiments, cells on the CryoArray are detected or quantified by probing the cryosections with a nucleic acid; this can also be used to identify cells or cell types, for instance using a ribosomal RNA probe. Nucleic acids can also be used to detect cells that possess a specific target sequence, for instance transformed cells that contain a recombinant molecule (e.g., a plasmid).

Cell-based CryoArrays can also be assayed using activity probes, which can be used for instance to identify transformed cells that express a marker, or to detect cells of a certain natural genotype, etc.

In other embodiments, cell-based CryoArrays can be loaded with cells harvested by laser capture microdissection (LCM). LCM enables the specific selection of identifiable cell types from within a tissue sample. Having identified and harvested specific cell type using LCM, cell-based CryoArrays can be used to detect or quantify proteins using antibodies, and can be used to detect or quantify a nucleic acid using a nucleic acid probe.

G. Delivery CryoArrays

It is also contemplated that cryosections can be used to deliver microorganisms (e.g., viruses, bacteria, or fungi) or cells (e.g., potentially neoplastic cells) to an organism, such as a laboratory research animal. By way of example, a number (e.g., 25–50) invasive bacterial or fungal strains are placed into an array. Individual cryosections from this delivery array are then implanted into the abdomen or subcutaneous tissue of a subject, for instance a laboratory animal such as a rat or a rabbit. Localized invasion by one or more of the arrayed strains could be detected, for instance by scanning technology or at autopsy. Replicates could be performed very easily, because the array can be used to generate additional cryosections. If a difference is noticed between different strains in their invasiveness (or in another characteristic observed in this system), the strains can be examined further to identify candidate proteins or other characteristics that account for observed differences.

Similarly, a plurality of tumor cells (e.g., from cell lines, biopsy samples, and so forth) could be placed into an array, and screened for invasion in animal model.

In delivery CryoArrays, the probe used to characterize a biological characteristic of the target cells on the array is the subject.

H. Virus-based CryoArrays

It is also contemplated that viruses can be placed into the wells of CryoArrays. Virus-based CryoArrays can be seen as overlapping with both protein-based and nucleic acid-based CryoArrays, as discussed above, because a virus array can be probed for the presence of either protein (e.g., viral coat protein) or nucleic acid. Thus, methods described above for detecting proteins or nucleic acids can be used to detect viruses in virus-based CryoArrays.

In specific embodiments, the CryoArray is loaded with a phage display library, and the cryosections are assayed for the presence (or absence) of particular desired display component proteins, for instance using antibodies or proteins that interact with the displayed protein component.

Viruses could also be used to construct a delivery CryoArray, in that virus samples could be placed into the array, and cryosections from that array placed into a subject (e.g., a research animal). Biological effects from the viruses could be examined, including tissue/cell invasion, lysis, and interaction with specific cell types or proteins.

I. Sample-Based CryoArrays

CryoArrays can also be used to perform parallel analyses of biological or other samples, particularly samples that are or can be suspended in a fluid. Such samples include, for instance, serum or other blood-derived products, including buffy coat, urine, urinary casts, amniocentisis samples, sweat, tears, semen, mucous, saliva and spit. In addition, samples taken from the environment (e.g., water, soil, or air samples), swab samples taken from surfaces (for instance, to check for microbial contamination), and the like, can also be used to generate samples analyzed in a CryoArray. Where such samples are not fluid, they can be suspended in fluid in order to enable injection of the sample into the cryoblock.

CryoArrays can be used, for instance, to detect the presence (or absence, or quantity) of a specific protein (e.g., an antibody or antigen), a specific nucleic acid (e.g., a nucleic acid characteristic of a disease state or infection), or a cell or virus in the sample.

In specific sample-based CryoArray embodiments, the fluid samples placed into the array are probed for one or more biomarkers (e.g., cancer biomarkers, disease biomarkers, etc.), in order to determine if the subject from whom the biological samples are taken are susceptible to (or suffering from) a disease or condition that is linked to the biomarker.

Sample-based CryoArrays that contain biological or other fluid samples can also be probed with specific antibodies, for instance in order to detect the presence of a contaminating bacteria or disease organism.

Enzyme activity can also be assayed in sample-based CryoArrays that contain fluid samples, for instance biological fluid samples.

In some embodiments, the samples used to generate the CryoArray are processed prior to being loaded into the array, for instance by amplifying a rare nucleic acid in the sample. Nucleic acids, whether amplified or not, can be detected for instance using in situ hybridization within the arrays. In some embodiments, the nucleic acids are amplified after they are placed into the array, for instance using in situ RT/PCR.

V. Application of Targets to Arrays

After a target preparation (sample) is produced, the target can be deposited into the array block using, for instance, injection into the wells of the cryoblock. Samples are usually fluid, or suspended in a fluid, so that they can readily be injected into the sample wells in the cryoblock. After the samples are injected into the array block, they are frozen (solidified sufficient to facilitate sectioning) into the block; this will in some embodiments occur essentially simultaneously with injection of the sample, due to the temperature of the cryoblock.

The fluid suspension in which a sample is applied to the CryoArray can be supplemented with one or more conditioning compounds. Such conditioning compounds can, for instance, be used to enable the sample to bind more fully to the substrate of the cryoblock, or to stabilize the target molecules or cells within the sample. For instance, conditioning compounds can be used to adjust the osmolarity or osmolality of the sample, to adjust the pH or salt concentration, to increase the rigidity or flexibility of the sample fluid upon freezing, or to stabilize the target molecule or cell. Gelling agents can be added, which in some embodiments and with some cryoblock substrates will facilitate binding of the sample to the cryoblock substrate upon freezing.

It is particularly envisioned that cell preservative compounds may be added to samples in those embodiments where whole, viable cells are applied as targets in the array. Such preservative compounds, such as sugars (e.g., trehalose) or glycerol, can provide stability to the whole cells during the freezing process and will facilitate viability of the cells after the array is loaded and sectioned.

Dispensing of samples into a CryoArray can be automated. For instance, a dispenser can move from address to address, depositing only as much target as necessary into each well. Examples of automated dispensers include a robotic system to control the position of a micropipette with respect to the cryoblock. In other embodiments, the dispenser includes a series of tubes, a manifold, an array of pipettes, or the like so that multiple targets can be delivered to the wells simultaneously. For CryoArrays with relatively few samples, or customized CryoArrays, samples can be manually injected into the wells in the cryoblock.

In some embodiments, it is desirable to be able to correlate a signal from one or more features of a CryoArray to the level of one or more target molecules on the array. Absolute quantitation can be accomplished by inclusion of known concentrations of one or more target molecules (for example control nucleic acids or proteins, or with a known amount the target nucleic acids or proteins themselves) and referencing the probe signal intensity of unknowns with the known targets (for example by generation of a standard curve). This can be done by including in the CryoArray samples containing known target levels (e.g., concentrations) as internal standards. Control samples can be placed in any of the sample wells within the array, though it is particularly envisioned that control samples would be placed along one row (or column) of sample wells, or at a corner, or in some other recognizable pattern within the array.

By way of example, in some embodiments, genes or proteins (e.g., yeast genes or proteins) can be applied to the array as internal control. Control genes or proteins are selected such that a probe directed to them (e.g., a hybridizing oligonucleotide or an antibodies) does not bind target molecules from the organism from which the test samples have been generated (e.g., mammalian genes or proteins).

VI. Sectioning CryoArrays

CryoArrays are produced as a three-dimensional block, as illustrated in FIGS. 1, 2, 3, and 4, for instance. It is generally contemplated that "sections" or "slices" will be removed from the cryoblock, substantially perpendicular to the long access of the sample wells in the block, prior to the array being assayed for the presence or absence (or quantity) of a target molecule. Depending on the thickness of the cryoblock used to produce the array, and the thickness of the sections removed to produce individual cryosections, up to a few hundred sequential cryosections can be made from a single cryoblock. In some embodiments, including the specific embodiment described in the Example, sections are each about 10 $\mu$M thick. However, thicker sections can be used, for instance 15 $\mu$M, 20 $\mu$M, 25 $\mu$M, 50 $\mu$M, 75 $\mu$M, or even 100 $\mu$M, or more; thicker sections are beneficial, for instance, in embodiments wherein assaying the target molecules occurs in the array section itself, rather than after transfer of the array to a transfer substrate surface. In some embodiments, thinner sections are used, for instance sections 2 $\mu$M, 3 $\mu$M, 4 $\mu$M, 5 $\mu$M, 6 $\mu$M, or 8 $\mu$M thick.

Methods for sectioning a block of tissue or samples in a frozen embedding compound are well known. By way of example, sections can be removed from a CryoArray using a microtome. In embodiments that employ thicker sections, a vibrotome can be used, though it should be kept cold in order to maintain the temperature of cold CryoArray blocks.

VII. Transferring of Cryosections

CryoArray sections are relatively thin, as discussed above. Transfer of a cryosection to a transfer substrate surface can be facilitated by contacting the cryosection with an adhesive surface, for instance a piece of cellophane or plastic tape or other surface that is adherent on one side (e.g., a sticker, non-cellophane tape, and so forth) or both sides (e.g., a double-sided tape, such that an adhered cryosection can be "attached" to another surface using the adhesive on the "back" of the tape). Adhering a cryosection to tape or another sticky surface is also useful in those embodiments where a probe assay is performed on the cryosection itself, as the adhering surface provides support and stability to the cryosection.

In some embodiments, the cryosection is used directly in one or more analyses, as described more fully herein. In other embodiments, the cryosection (or at least a portion of the samples contained within the cryosection) is transferred to a transfer substrate surface for further analysis. Transfer can involve passive transfer of molecules from the surface of the cryosection to the transfer substrate surface through direct contact. Transfer need not be "complete," in that the entire amount of target molecules contained in the cryosection need not be moved from the cryosection to the transfer substrate surface. Usually, only enough of the target molecules need transfer to provide a detectable amount for assaying.

Transfer of some or all of the contents of a cryosection produces a replica of the CryoArray on the transfer substrate surface. As described herein, methods of detecting targets in a CryoArray section refer also to detecting targets in replicas of the section, particularly replicas produced by transfer.

Examples of transfer substrates to which constituents of the disclosed CryoArray sections can be transferred include glass (e.g., functionalized glass), Si, Ge, GaAs, GaP, $SiO_2$, $SiN_4$, modified silicon nitrocellulose, polyvinylidene fluoride, polystyrene, polytetrafluoroethylene, polycarbonate, nylon, fiber, or combinations thereof. Array substrates can be stiff and relatively inflexible (e.g., glass or a supported membrane) or flexible (such as a polymer membrane). One commercially available microarray system that can be used with the arrays is the FAST™ slides system (Schleicher & Schuell, Dassel, Germany), which incorporates a patch of polymer on the surface of a glass slide.

It is contemplated that a portion of the cryoblock substrate itself may also transfer to the transfer substrate surface. This can be beneficial, in that it can in some instances serve as a blocking agent on the transfer substrate surface during subsequent probing of the array.

VIII. Array Probes

Many different probe molecules can be used with the arrays and methods disclosed herein. Probes can be selected, for example, based on the needs of an individual investigator.

Though in many embodiments a single type of probe molecule (for instance one protein or one nucleic acid) will be used at a time to assay the array, in some embodiments, mixtures of probes will be used simultaneously, for instance mixtures of two proteins or two nucleic acid molecules. Simultaneous multiple-probing (e.g. double-probing) can be used to detect, for instance, competitive binding or binding systems that require the interaction of more molecules than just one polypeptide target and one probe molecule. Simultaneous multiple-probing can also be used to detect a control target and a test target at the same time on the same array. It is preferred that probes used simultaneously on the same array are detectably different so that the presence of one or the other probe (or both) at a feature on the array can be distinguished.

A. Probes for Detecting Proteins

Any molecule that might bind to or interact with one or more polypeptides that is or may be on the CryoArray can be used as a probe. In specific embodiments, probes are from different molecular classes (e.g., nucleic acids, oligo- or polypeptides, or various types of ligands). Probes (especially those that are polymeric chains) may be of various lengths, and different results may be obtained from the same array by using related probe molecules of different length. Likewise, varying the sequence of polymeric chain probes may provide valuable binding data.

In some embodiments, wherein the features of the array contain antibodies, and the binding specificity of the antibodies is being detected or measured, appropriate probes include antigenic molecules, such as proteins or protein fragments, known to or suspected of interacting with one or more of the antibodies. If the mere presence (or absence) of antibodies is being detected on the array, antibodies to the antibodies (for instance to a class of antibodies, e.g., anti-IgG, anti-IgM, etc.) are appropriate as probes.

Antibodies of course can be used as probes to detect the presence (or absence, or quantity) of polypeptide targets on the provided CryoArrays.

Wells in the CryoArray can be "spiked" with a positive control protein molecule that is not expected to otherwise be present in ANY of the target samples; this positive control can be probed for simultaneously with the target, using probes that are differentially detectable. This provide not only a control for the binding process, but also it provides a way to monitor for loss of sample from the cryosection (e.g., samples have been displaced from (fallen out of) the cryosection wells, or bubbles in the cryoblock wells).

B. Activity-Based Probes

In certain embodiments of the provided CryoArrays, an activity of a target on the array is assayed; probes in such embodiments are considered activity-based probes because they are used to assess the activity of a target. These embodiments are made possible because the CryoArrays are produced at a low temperature (e.g., at or near freezing); the low temperature at which the arrays are manufactured helps protect the biological activity of samples in the array, such as proteins.

Thus, it is contemplated that CryoArray sections can be assayed for a biological activity, for instance the activity of a protein, of a target molecule in one or more features using an activity-based probe that is a substrate of that biological activity (which substrate may contain a label, as discussed herein), or a probe that is a reporter system that interacts with the target to produce a detectable signal. In specific examples of the provided CryoArrays, the probe is a substrate for one or more target proteins in features on the array, and the presence of such protein(s) is detected (and/or quantified) by examining a change in the substrate or in a product of the activity of the protein in the presence of the substrate. Similarly, in some embodiments where cells (e.g., bacterial or yeast cells) form the features, some probes are assay systems upon which the cells (or constituents within the cells) perform a biological reaction, which reaction produces a detectable signal. For instance, if the cells in the array have been transformed with a construct that may express a gene from a reporter system (e.g., the β-gal system or another such research system), then the components of the reporter system would form a probe useful in assaying the array to detect expression.

In some embodiments, the reagents necessary to carry out an activity assay on a cryosection are localized to the region adjacent to the cryosection surface by incorporating the reagents into a matrix, such as a gelatin, agarose, or acrylamide based matrix.

C. Probes for Detecting Nucleic Acids

Similarly to detecting proteins, nucleic acids can be detected using a variety of different probes. Such probes include nucleic acid molecules (e.g., oligonucleotides) that hybridize specifically to the target nucleic acid, proteins that interact with the target nucleic acid (e.g., DNA binding proteins), and so forth. Probes can be single molecules (e.g., a purified single species of oligonucleotide, used to detect the presence or absence of a specific target nucleic acid in one or more feature on the array). Probes also can be mixtures of molecules (e.g., a mixture of cDNAs reflecting cellular expression in a cell sample, used to interrogate an array that contains defined individual nucleic acids at individual features—similar to the system used with a cDNA microarray).

A hybridization probe for use in certain CryoArrays may be referred to as a sequence "representing" a particular gene or gene product. A sequence "representing" a particular gene product is one that will specifically hybridize to a nucleic acid molecule encoding that gene product, thereby permitting identification of that gene product. Such sequences representing a particular gene product may include an entire cDNA sequence (or the corresponding genomic gene sequence) or less than an entire cDNA sequence. For example, the probe may include an oligonucleotide comprising a minimum specified number of consecutive bases of a selected gene that is differentially expressed. Oligonucleotides as short as 8–10 consecutive bases of a cDNA will be effective to produce meaningful gene expression data using microarray technology. For enhanced specificity of hybridization, longer oligonucleotides may be employed, such as at least 10, 15, 20, 25, 30, 50, 50 or more consecutive bases of a cDNA. Other examples of probe molecules that are shorter than the full length of the subject cDNA include individual exons of the gene sequence of interest, ESTs from within the gene sequence, or regions of the nucleotide sequence of interest that encode conserved regions within the encoded proteins (and thereby may be useful to examine the expression of related proteins). In the latter example, it will be advantageous in certain embodiments to produce a collection of degenerate probe molecules; the production of such degenerate probes is known.

Furthermore, a probe "representing" a particular gene product need not be a perfect match for the sequence of that gene. Typically, such probes will share at least 70% sequence identity with the corresponding cDNA, but probes sharing at least 75%, 80%, 85%, 90%, 95%, 97%, 98%, and 99% sequence identity may be utilized to achieve enhanced specificity.

In many embodiments, it is beneficial to prepare a probe molecule for use as a control in analyzing nucleic acids on a CryoArray. Positive probe standards include any probes that are known to interact with at least one of the nucleic acids of the array, which may be found in certain spots, or in all spots on the array. Negative probe standards include any probes known not to interact with any nucleic acid sequence contained in at least one mixture of nucleic acids (contained in a spot) of the array. Positive control probe sequences could, for instance, be designed to hybridize with a so-called "housekeeping" gene, which is known to or suspected of maintaining a relatively constant expression level (or at least known to be expressed) in a plurality of cells, tissues, or conditions. Many of such "housekeeping" genes are well known; specific examples include histones, β-actin, or ribosomal subunits (either mRNA encoding for ribosomal proteins or rRNAs). Alternatively, wells in the CryoArray can be spiked with a positive control nucleic acid molecule that is not expected to otherwise be present in ANY of the target samples; this positive control can be probed for simultaneously with the target, using probes that are differentially detectable. Not only does this provide a control for the hybridization process, it also provides a way to monitor for loss of sample (e.g., samples have been displaced from (fallen out of) the cryosection wells, or bubbles in the cryoblock wells).

IX. Labeling and Detection of Probe Molecule(s)

Usually, probe molecules used to assay the disclosed arrays are detectable. In some embodiments, probes are detectable based on their inherent characteristics (e.g., immunogenicity) or can be rendered detectable by being labeled with an independently detectable tag. Probes can be rendered detectable by being labeled with an independently detectable tag or other reporter molecule. Such tags include fluorescent or luminescent molecules that are attached to the probe, or radioactive monomers or other detectable molecules that can be added during or after synthesis of the probe molecule. Other tags may be immunogenic sequences (such as epitope tags) or molecules of known binding pairs (such as members of the strept/avidin:biotin system). Still other tags and detection systems are known to those of skill in the art, and can be used in the present invention.

Labeling different probes with different tags, each of which can be detected simultaneously (e.g., two fluorophores that fluoresce at different wavelengths) enables simultaneous detection of hybridization of two or more probes on the nucleic acid mixtures of an array. Multiple-label challenges to an array can also be used to provide an internal control. For competitive binding assays, however, only one of the probes needs to be detectable. The detectable label (e.g., the fluorophore) may be incorporated during synthesis of the probe.

It will be appreciated that the color of the labels used is not critical, so long as the emission wavelength of the different fluorophores used can be resolved, and can be used to measure differential expression. Other fluorophores or labels can be used to practice the disclosed methods.

In some embodiments, detection involves either single-color fluorescence hybridization to measure the levels of expression of a single gene in all of the arrayed specimens, or two-color fluorescence hybridization to examine the relative expression of genes of two different genes simultaneously, or to provide an internal (e.g., quantitative) control for the detection of expression of a single gene.

For single-color fluorescence hybridization experiments, a probe molecule corresponding to a gene of interest is produced. The probe is labeled, for example using a fluorescent dye such as Cy3 or Cy5 (Amersham Pharmacia Biotech, Piscataway, N.J.), or any other fluorophore or label. The label can be incorporated directly during synthesis. The probe is then hybridized to the array. Following washing to remove non-specifically bound probe, the array is scanned for fluorescent emission following laser excitation, and the intensity of each fluorescing spot is measured. The intensity of each spot is approximately proportional to the expression of the gene (corresponding to the probe) in each nucleic acid mixture contained within a spot on the array. This data provides an indication of the expression of a particular gene (corresponding to the labeled probe) in the specimens (e.g., cells or tissues) from which the mixtures of nucleic acids were prepared.

For two-color fluorescence hybridization experiments, two probe molecules are produced and labeled as described above, except that each probe is labeled with a different fluorescent label, each of which fluoresces at a different wavelength (for example, one sample may be labeled with Cy3 and the other with Cy5). After the two probe preparations are labeled, they are mixed together and hybridized to a single array. Alternatively, they can be applied to the single array sequentially in certain embodiments. After washing, the array is scanned using two fluorescence channels. Because the two fluorescent labels are selected such that their emission spectra do not overlap, the signal of each of the two fluors can be measured for each of the probes. The absolute levels of intensity for each probe in an array is approximately proportional to the expression of the gene in the sample examined, and the ratio of the two fluor intensities indicates the relative expression of a gene in the two different samples.

Where one of the probes used in a two-color experiment is used as a control, and is directed toward a "housekeeping" gene, its signal intensity at each spot can be used to normalize the hybridization signal intensity of the test probe at each corresponding spot.

X. Computer Assisted (Automated) Detection and Analysis

The data generated by assaying a CryoArray can be analyzed using known computerized systems. For instance, the array can be read by a computerized "reader" or scanner and quantification of the binding of probe to individual addresses on the array carried out using computer algorithms. Likewise, where a control probe has been used, computer algorithms can be used to normalize the hybridization signals in the different spots of the array. Such analyses of an array can be referred to as "automated detection" in that the data is being gathered by an automated reader system.

In the case of labels that emit detectable electromagnetic wave or particles, the emitted light (e.g., fluorescence or luminescence) or radioactivity can be detected by very sensitive cameras, confocal scanners, image analysis devices, radioactive film or a Phosphoimager, which capture the signals (such as a color image) from the array. A computer with image analysis software detects this image, and analyzes the intensity of the signal for each probe location in the array. Signals can be compared between spots on a single array, or between arrays (such as a single array that is sequentially probed with multiple different probe molecules), or between the labels of different probes on a single array.

Computer algorithms can also be used for comparison between spots on a single array or on multiple arrays. In addition, the data from an array can be stored in a computer readable form.

Certain examples of automated array readers (scanners) will be controlled by a computer and software programmed to direct the individual components of the reader (e.g., mechanical components such as motors, analysis components such as signal interpretation and background subtraction). Optionally software may also be provided to control a graphic user interface and one or more systems for sorting, categorizing, storing, analyzing, or otherwise processing the data output of the reader.

To "read" an array, an array (or replication thereof) that has been assayed with a detectable probe to produce binding (e.g., a binding pattern) can be placed into (or onto, or below, etc., depending on the location of the detector system) the reader and a detectable signal indicative of probe binding detected by the reader. Those addresses at which the probe has bound to an immobilized nucleic acid mixture provide a detectable signal, e.g., in the form of electromagnetic radiation. These detectable signals could be associated with an address identifier signal, identifying the site of the "positive" spot. The reader gathers information from each of the addresses, associates it with the address identifier signal, and recognizes addresses with a detectable signal as distinct from those not producing such a signal. Certain readers are also capable of detecting intermediate levels of signal, between no signal at all and a high signal, such that quantification of signals at individual addresses is enabled.

Certain readers that can be used to collect data from the arrays, especially those that have been probed using a fluorescently tagged molecule, will include a light source for optical radiation emission. The wavelength of the excitation light will usually be in the UV or visible range, but in some situations may be extended into the infra-red range. A beam splitter can direct the reader-emitted excitation beam into the object lens, which for instance may be mounted such that it can move in the x, y and z directions in relation to the surface of the array substrate. The objective lens focuses the excitation light onto the array, and more particularly onto the (polypeptide) targets on the array. Light at longer wavelengths than the excitation light is emitted from addresses on the array which contain fluorescently-labeled probe molecules (i.e., those addresses containing a target molecule to which the probe binds).

In certain embodiments, the array may be movably disposed within the reader as it is being read, such that the array itself moves (for instance, rotates or moves laterally) while the reader detects information from each address. Alternatively, the array may be stationary within the reader while the reader detection system moves across or above or around the array to detect information from the addresses of the array. Specific movable-format array readers are known and described, for instance in U.S. Pat. No. 5, 922,617, hereby incorporated in its entirety by reference. Examples of methods for generating optical data storage focusing and tracking signals are also known (see, for example, U.S. Pat. No. 5,461,599, hereby incorporated in its entirety by reference).

For the electronics and computer control, a detector (e.g., a photomultiplier tube, avalanche detector, Si diode, or other detector having a high quantum efficiency and low noise) converts the optical radiation into an electronic signal. An op-amp first amplifies the detected signal and then an analog-to-digital converter digitizes the signal into binary numbers, which are then collected by a computer.

XI. Kits

CryoArray sections (cryosections, loaded with samples) and CryoArray blocks (either pre-loaded or unloaded/ "empty") can be supplied in the form of a kit for use in various analyses. In such a kit, at least one CryoArray section or CryoArray block is provided. The kit also includes instructions, usually written instructions, to assist the user in generating and/or probing the array. Such instructions can optionally be provided on a computer readable medium.

Some provided kits are kits for making CryoArrays. Such kits can include a cast form (e.g., in aluminum or other material) in which an array block is cast, with or without a well form array (e.g., a block of needles or pins that are inserted into the block substrate to form the sample and/or orientation wells). Some kits will also include a block punch, for pushing the formed array block out of the cast form; such block punches can be made to have an end profile slightly smaller than and in the same shape as the cross section of the hole in the cast form in which the CryoArray block is molded. Kits can also include an array substrate, such as an amount of embedding compound; array substrate may be provided in the kit in an amount such that more than one array can be generated using the provided substrate. In other embodiments, the mold in which the sample block is formed disassembles or can otherwise be released from the frozen block (for instance, with a spring-loaded aluminum frame rather than a solid frame, much like a springform cake pan or springforms used in forming concrete).

In kits that provide one or more prepared CryoArray sections, these sections can be provided already transferred to a transfer substrate surface, such as a slide or membrane. Alternatively, sections in some kits are provided adhered to a surface using a two-sided adhesive, such as double-sided tape, such that the array is "right side up" (rather than reversed, as usually occurs with transfer to a transfer substrate surface).

Kits may additionally include one or more buffers for use during assay of sections of the provided array. For instance, such buffers may include a low stringency wash, a high stringency wash, and/or a stripping solution. These buffers may be provided in bulk, where each container of buffer is large enough to hold sufficient buffer for several probing or washing or stripping procedures. Alternatively, the buffers can be provided in pre-measured aliquots, which would be tailored to the size and style of CryoArray included in the kit.

Certain kits may also provide one or more containers in which to carry out array-probing reactions, slides onto which cryosections can be placed, tape or the equivalent for transfers of cryosections, and so on.

Kits may in addition include either labeled or unlabeled control probe molecules, to provide for internal tests of either the labeling procedure or probing of the gene profiling array, or both. The control probe molecules may be provided suspended in an aqueous solution or as a freeze-dried or lyophilized powder, for instance. The container(s) in which the controls are supplied can be any conventional container that is capable of holding the supplied form, for instance, microfuge tubes, ampoules, or bottles. In some applications, control probes may be provided in pre-measured single use amounts in individual, typically disposable, tubes, or equivalent containers.

The amount of control probe(s) supplied in the kit can be any particular amount, depending for instance on the market to which the product is directed. If the kit is adapted for research or clinical use, sufficient control probe(s) likely will be provided to perform several controlled analyses of a CryoArray. Likewise, where multiple control probes are provided in one kit, the specific probes provided usually are tailored to the market and the accompanying kit. In certain embodiments, a plurality of different control probes will be provided in a single kit, each control probe being from a different type of specimen found on an associated array (e.g., in a kit that provides both eukaryotic and prokaryotic specimens, a prokaryote-specific control probe and a separate eukaryote-specific control probe may be provided). Positive and negative control probes both may be provided.

Where the kit is a kit for producing a CryoArray, and the user may elect among different types of samples to be loaded into the array, the kit may include different control probes for the different types of samples (e.g., nucleic acids, proteins, antibodies, cells, viruses, etc.). Likewise, in such kits there may be included one or more control samples to be placed into the array block (or already present in a pre-fabricated array block) to serve as control features, where the remainder of the features are provided by the user.

In some embodiments, kits may also include reagents necessary to carry out one or more probing and/or probe-labeling reactions. The specific reagents included will be chosen in order to satisfy the end user's needs, depending on the type of probe molecule (e.g., protein, nucleic acid, activity assay) and the method of labeling (e.g., radiolabel incorporated during probe synthesis, attachable fluorescent tag, etc.).

Further kits are provided for the labeling of probe molecules for use in assaying arrays provided herein. Such kits may optionally include an array to be assayed by the so-labeled probe molecules. Other optional components of such kits are largely as described above for kits for constructing or assaying a CryoArray.

The invention is illustrated by the following non-limiting Example.

EXAMPLE 1

Preparation and Probing of CryoArray Block

This example provides methods for making and using a CryoArray, wherein the samples on the array comprise proteins.

Fabrication of CryoArrays. CryoArrays were formed from several different substrates, including Jell-O™, polyacrylamide, and histologic embedding compound (TissueTek OCT, Sakura, Torrance, Calif.; OCT, CryoGel, Instrumedics Inc., Hackensack, N.J.) as follows: a 12×19× 12 mm aluminum mold (NIH Design Service) was filled with the substrate and into the mold was inset a 5×5 array of 23 gauge needles, spaced 2 mm apart, protruding 1 cm from an aluminum block (FIG. 5A), to form the sample wells shown in FIG. 5B. The sample block was frozen on dry ice, then placed in a thermostatically controlled cooling chamber (Boekel Scientific, Feasterville, Pa.) set at −5° C. After the block reached −5° C., the needle array was removed. The sample block was removed from the aluminum mold by pushing it out with a punch (also of aluminum) milled to fit the hole in which the block was formed. A snug fit on the punch was used to facilitate maintenance of the geometry of the block, and to avoid distortion as the block was removed from the mold.

Filling/Loading a CryoArray Block. Biological samples were prepared from tissue homogenates or body fluids (urine, serum), and contained 0–20% sucrose and 0–15% colored gelatin (final concentration). The wells of the CryoArray were filled with biological samples using a 10 μl glass syringe (Hamilton Company, Reno, Nev.) (FIG. 5B). The samples froze and bonded to the cryoblock because of the temperature of the block.

Sectioning CryoArrays: Next, 10 μm sections of the CryoArrays were cut on a cryostat and transferred to nitrocellulose membranes (Trans-blot (BioRad, Hercules, Calif., with or without an enhancer) or nitrocellulose-coated slides (FAST™ slides, Schleicher & Schuell Inc., Keene, N.H.) using Scotch tape (FIG. 5C) (Scotch Magic Transparent Tape, 3M Company, St. Paul, Minn.). The tape-transfer system preserved the geometry of the array.

The sections were dried for 30 minutes at room temperature under continuous air flow using a fan. The tape was carefully removed, allowing the OCT section to adhere to the nitrocellulose membrane (FIG. 5D). Sequential sections could be tested for protein expression by immunohistochemistry or protein function by direct assay. Each spot contained approximately 0.7 nl of sample.

Solutions. CryoArrays were filled with fluorescein-labeled IgG (0.01–0.2 mg/ml, Molecular Probes Inc., Eugene, Oreg.), recombinant human prostate specific antigen (PSA, 0.1 ng/μl, Scripps Laboratories, San Diego, Calif.), or kidney homogenate (0.5–30 mg/ml). Fluorescein-labeled IgG was imaged using a Multi Image Light Cabinet (Alpha Innotech Corp., San Leandro, Calif.).

Detection of a Purified Protein Antigen: Antigens were detected using an anti-PSA antibody (DAKO Corp., Carpinteria, Calif.). The primary antibody was applied at a dilution of 1:600 overnight at 4° C. in a CoverWell Incubation Chamber (22×40×0.2 mm, Electron Microscopy Sciences, FT. Washington, Pa.). The primary antibodies were detected using EnVision plus system (DAKO Corp.).

Statistics. All data are presented as mean±standard deviation. Statistical analysis was performed using correlation analysis (Microsoft Excel).

Results

Design/Fabrication Optimization. One goal of this characterization was to achieve reproducible CryoArrays, where sequential cryosections had sample spots that were uniform and reproducible, with preserved geometry. In initial fabrication trials, it was determined that the sample block performs optimally if it is easy to cut, and the samples adhere to the block during the cutting process.

Cryoblocks were fabricated from TissueTek OCT, Jell-O™, polyacrylamide, and CryoGel OCT. The samples did not adhere to TissueTek OCT or polyacrylamide, despite adding bis to the samples. Jell-O™ was less suitable because the geometry of the array became distorted upon freezing, and frozen Jell-O™ was suboptimally soft to section reliably. In contrast, CryoGel OCT produced a solid block that was easy to cut on a cryostat, and to which samples could be easily bonded in the sample wells.

Figure 6A:
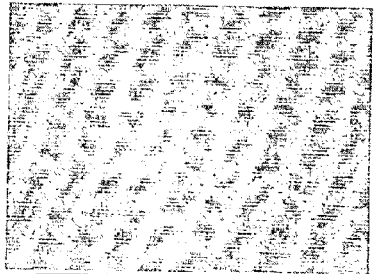
FIG. 6A shows the signals produced when samples are loaded into the cryoblock without sucrose or gelatin. The cryosection was pressed against a nitrocellulose membrane, and the fluorescent labeled protein that transferred to the membrane is shown, rather than the array itself.

Preliminary CryoArrays were produced by bonding the samples to the OCT block by melting than re-freezing the sample block. The block was formed on dry ice, then warmed to −5° C. The samples (in liquid form) were injected at −5° C., then the block was melted by warming the block to +4° C., then rapidly re-freezing it on dry ice. This method was effective at bonding samples to the block, but it subjected the samples to an additional thaw/freeze cycle and tended to cause air-bubble formation in samples and throughout the block. In addition, CryoArray samples on sections produced from blocks made with this freeze-thaw method were smeared, displayed non-uniform spot size, and showed considerable spot to spot variability (FIG. 6A). The smearing was found to be caused by the tape transfer system, and disappeared when sections were completely dried on the transfer membrane and the tape was removed slowly and carefully after transfer was complete.

Figure 6B:
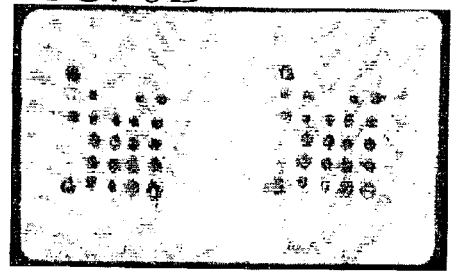
FIG. 6B shows the signals produced when samples containing sucrose are loaded into the cryoblock.
Figure 6C:
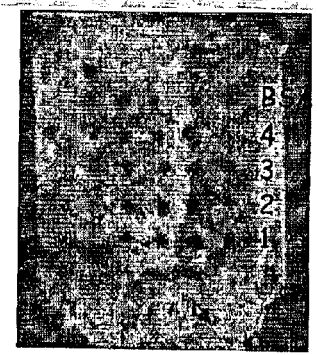
FIG. 6C shows the signals produced when samples containing both sucrose and gelatin are loaded into the cryoblock. Key: row 1, 0.5 ng/μl recombinant PSA; row 2, 0.1 ng/μl; row 3, 0.02 ng/μl; row 4, 0.004 ng/μl; row "BSA," BSA rather than PSA as a negative control.
Figure 6D:
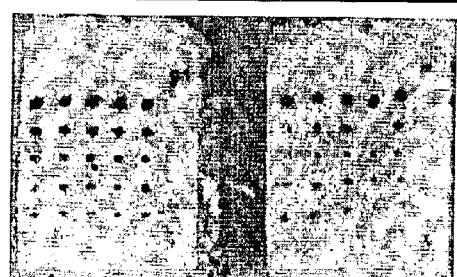
FIG. 6D illustrates that the integrity of signals from a CryoArray section is improved when the thaw and refreeze cycle is omitted (left-hand panel).

The non-uniformity and variability of spots was determined to be linked to sample "spots" dropping out of the arrays because the freezing did not yield uniform bonding to the recipient array. Since CryoGel OCT contains 80% water, 10% sucrose, and 10% proprietary materials, the osmolality of the samples was balanced by adding 20% sucrose to the samples. This enhanced the reproducibility signal intensity from individual samples in cryosections, but the apparent feature spot size was still highly variable (FIG. 6B). Without intending to be limited to a single possible explanation, it was hypothesized the variability in feature size was caused by diffusion of sample in to the block. To reduce such diffusion, 15% colored gelatin (Jell-O™) was added to the samples before they were injected into the wells of the recipient array. This enabled better annealing of samples to block (FIG. 6C), and eliminated the need for the thaw/re-freezing steps. Subsequent arrays were produced with 20% sucrose and 15% colored gelatin. The color marker (e.g., orange Jell-O™) also allowed easier filling of the sample wells.

For these reasons, the array is ideally (although not necessarily) maintained below freezing while the samples are placed in the array and frozen into the substantially solid substrate.

Figure 7A:
FIG. 7 shows protein transferred to three different capture membranes. A CryoArray block was filled with 0.5 pg/μl–0.5 ng/μl of recombinant human PSA. Sequential 10 μm sections were removed and transferred using Scotch tape to (FIG. 7A) Trans-blot membrane, (FIG. 7B) Enhancer membrane, and (FIG. 8C) FAST™ slides. The signal of the transferred protein was detected using a gel documentation system.
Figure 7B:
Figure 7C:
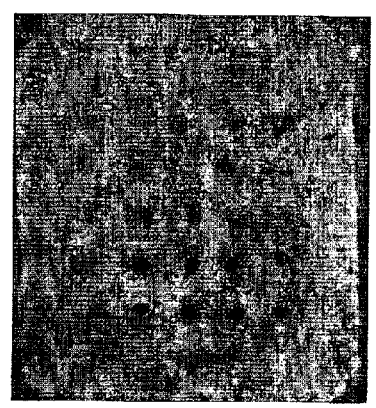

Transfer Membrane. The recovery of fluorescent IgG was tested using three different types of capture membranes:

Trans-blot (BioRad, Hercules, Calif.) attached to a glass slide, Enhancer membrane (Geno Technology Inc., St. Louis, Mo.) attached to a glass slide, and FAST™ slides (Schleicher &Schuell Inc), which contain a patch of nitrocellulose membrane bonded to the surface of a slide. The FAST™ slides had the best recovery of protein, based on signal intensity (FIG. 7).

Figure 8A:
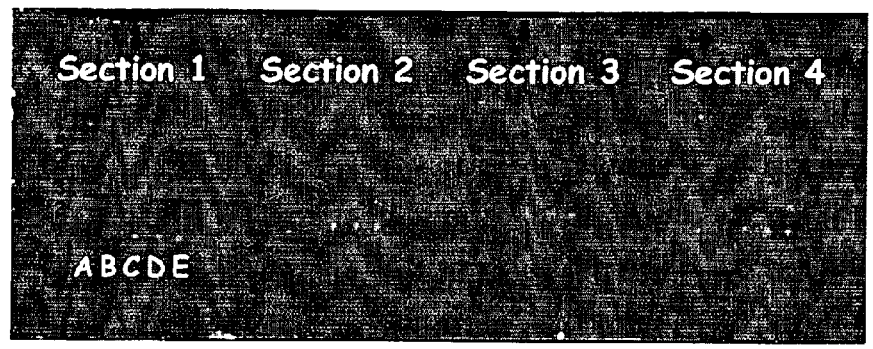
FIG. 8A shows the fluorescent signals from four sequential cryosections; the level of signal from the wells designated 1A through 1E are shown in FIG. 8B for each of the four sections.
Figure 8B:
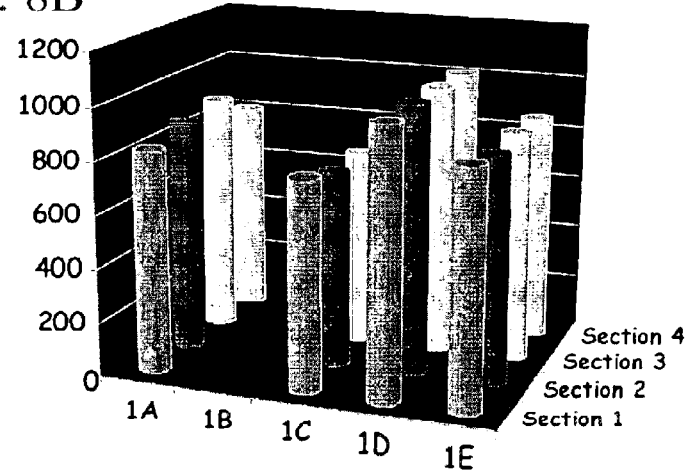
FIG. 8 illustrates the reproducibility of signals from individual cryosections of a CryoArray, using fluorescent-labeled IgG. Sample wells were filled with fluorescent-labeled IgG in 20% sucrose, and signal detected a gel documentation system. The illustrated experiment employed a round of thaw and re-freezing to bind samples to the cryoblock; omitting this cycle has been shown to increase reproducibility even further.
Figure 9A:
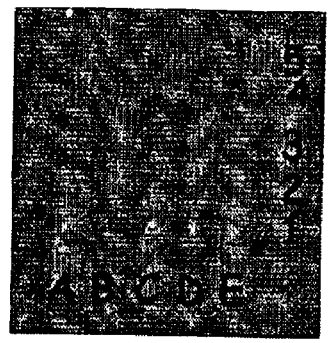
FIG. 9 illustrates the linearity of signal detected from features of a CryoArray, using fluorescently-labeled IgG. Sample wells were filled with 0.03–0.4 mg/ml fluorescently-labeled IgG, and signal (FIG. 9A) detected using a gel documentation system. The relative fluorescent signals (arbitrary units) from individual features at the indicated concentrations of fluorescently-labeled IgG are shown in FIG. 9B.
Figure 9B:
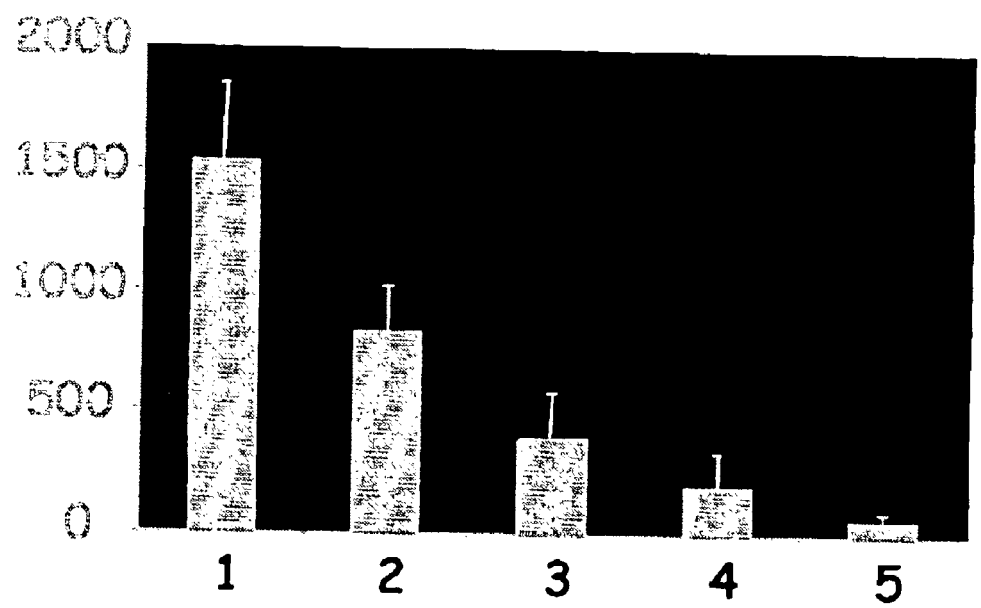

Reproducibility and Linearity. The reproducibility and linearity of the CryoArray system was tested using a cryoblock filled with samples that contained different concentrations of fluorolabeled-1gG (0.01–0.2 mg/ml, FIGS. 8 and 9).

The fluorescent signal from cryosections transferred to FAST slides was reproducible (coefficient of variation 3.6–10.1%), and linear over a 16-fold concentration range ($R^2=0.94$).

The ability of the CryoArray system to detect both recombinant and native proteins was examined by modified immunohistochemical methods. Recombinant human PSA (0.1 ng/$\mu$l) could be detected using an anti-PSA antibody with a detection limit of 0.3 pg/spot.

This disclosure provides methods for making and using CryoArrays for the parallel analysis of samples, including purified or mixed protein or nucleic acid samples, biological samples, cells, viruses, and so forth. The disclosure further provides CryoArrays produced by the described methods, including CryoArrays that are prepared and maintained at a temperature at, near or below freezing throughout their construction. It will be apparent that the precise details of the methods described may be varied or modified without departing from the spirit of the described invention. We claim all such modifications and variations that fall within the scope and spirit of the claims below.

We claim:

1. A method of making a CryoArray, comprising:
   providing a substrate having a plurality of sample wells;
   placing one or more liquid biological samples in one or more of the sample wells, such that the biological samples are at addressable locations within the array;
   and freezing the biological samples in the sample wells to produce a loaded array, wherein the loaded array is the CryoArray.

2. The method of claim 1, wherein the substrate is maintained at or below freezing while the biological samples are placed in the sample wells and frozen.

3. The method of claim 1, wherein the biological samples are bonded to the substrate when the biological samples are frozen.

4. The method of claim 3, wherein the substrate is composed of a gel that bonds to the biological samples when the samples are frozen.

5. The method of claim 1, wherein the biological samples comprise an acellular biological substance, a suspension of cells, a suspension of viruses, a biological fluid, or an environmental sample.

6. The method of claim 5, wherein the biological samples comprise a suspension of cells, and the cells are animal cells, plant cells, protist cells, bacterial cells, fungal cells, or a mixture of two or more thereof.

7. The method of claim 5, wherein the biological samples comprise an aceilular biological substance, and the acellular biological substance comprises a protein, a nucleic acid, a lipid, a carbohydrate, or a mixture of two or more of these substances.

8. The method of claim 5, wherein the biological samples comprise a biological fluid, and wherein the biological fluid comprises blood, a blood product, urine, sweat, tears, saliva, spit, an amniocentesis sample, semen, or mucous.

9. The method of claim 1, wherein the sample wells are elongated and substantially parallel to each other.

10. The method of claim 9, wherein the sample wells are oriented substantially transverse to opposing surfaces of the substrate.

11. The method of claim 1, wherein freezing occurs at less than 0° C.

12. A CryoArray produced in the method of claim 1.

13. A CryoArray produced in the method of claim 5.

14. A CryoArray produced in the method of claim 6.

15. A CryoArray produced in the method of claim 7.

16. A CryoArray produced in the method of claim 8.

17. A method of making a cryosection, comprising: sectioning the CryoArray of claim 12, to form at least one cryosection, such that the biological samples are at addressable locations in the cryosections.

18. A cryosection produced by the method of claim 17.

* * * * *